US008503603B2

(12) United States Patent
Tancredi et al.

(10) Patent No.: US 8,503,603 B2
(45) Date of Patent: Aug. 6, 2013

(54) ADJUSTABLE SCANNER

(75) Inventors: Henry John Tancredi, Ottsville, PA (US); Edward Marandola, Gwynedd, PA (US); Frank Speranza, Warminster, PA (US); Omid Ebrahimi Kia, North Bethesda, MD (US)

(73) Assignee: Dental Imaging Technologies Corporation, Hatfield, PA (US)

( * ) Notice: Subject to any disclaimer, the term of this patent is extended or adjusted under 35 U.S.C. 154(b) by 161 days.

(21) Appl. No.: 12/918,558

(22) PCT Filed: Feb. 20, 2009

(86) PCT No.: PCT/US2009/034750
§ 371 (c)(1),
(2), (4) Date: Aug. 26, 2010

(87) PCT Pub. No.: WO2009/105695
PCT Pub. Date: Aug. 27, 2009

(65) Prior Publication Data
US 2011/0026669 A1    Feb. 3, 2011

Related U.S. Application Data

(60) Provisional application No. 61/030,222, filed on Feb. 20, 2008.

(51) Int. Cl.
*A61B 6/14* (2006.01)
(52) U.S. Cl.
USPC ............................................................. 378/39
(58) Field of Classification Search
USPC .................................... 378/38–40, 193–198
See application file for complete search history.

(56) References Cited

U.S. PATENT DOCUMENTS

| 5,355,398 A | 10/1994 | Nakano et al. ................... 378/39 |
| 5,448,610 A | 9/1995 | Yamamoto et al. .............. 378/19 |

(Continued)

FOREIGN PATENT DOCUMENTS

| EP | 1721574 | 11/2006 |
| JP | H06-181 | 1/1994 |

(Continued)

OTHER PUBLICATIONS

Office Action from the United States Patent Office for U.S. Appl. No. 12/524,403 dated Nov. 17, 2011 (8 pages).
Office Action from the State Intellectual Property Office of the People's Republic of China for Application No. 200980105314.5 dated May 2, 2012 (English Translation and Original, 12 pages).

(Continued)

*Primary Examiner* — Courtney Thomas
(74) *Attorney, Agent, or Firm* — Michael Best & Friedrich LLP

(57) ABSTRACT

For dental and facial imaging, a source of x-rays (14) or other penetrating radiation and a detector (20) are mounted opposite one another on a rotatable gantry (28), so that the head of the patient can be positioned between the source (14) and the detector (20), with the axis of rotation (36) of the gantry passing through the patient's head. The detector or the source are mounted so they can translate and/or pivot horizontally or vertically. The gantry is angulated so that the source or the detector may not be at the same height relative to the patient's head. The gantry can telescope, moving the source and the detector closer together or further apart. The collimator changes dynamically with the motion of the gantry and/or the source and detector to scan a smaller portion of the scan field.

19 Claims, 20 Drawing Sheets

(56) References Cited

U.S. PATENT DOCUMENTS

| | | | |
|---|---|---|---|
| 5,574,763 | A * | 11/1996 | Dehner ............................ 378/17 |
| 5,600,699 | A | 2/1997 | Suzuki et al. .................... 378/38 |
| 5,666,392 | A | 9/1997 | Ploetz ............................ 370/535 |
| 5,997,176 | A | 12/1999 | Fairleigh ....................... 378/196 |
| 6,055,292 | A | 4/2000 | Zeller et al. ..................... 378/21 |
| 6,118,842 | A | 9/2000 | Arai et al. ..................... 451/227 |
| 6,412,978 | B1 | 7/2002 | Watanabe et al. .............. 378/197 |
| 8,005,186 | B2 | 8/2011 | Lee ................................. 378/38 |
| 2001/0036246 | A1 | 11/2001 | Graumann ...................... 378/39 |
| 2002/0085681 | A1 | 7/2002 | Jensen .......................... 378/197 |
| 2004/0190678 | A1 | 9/2004 | Rotondo et al. ................. 378/38 |
| 2005/0254620 | A1 | 11/2005 | Shoji et al. ...................... 378/37 |
| 2006/0067464 | A1 | 3/2006 | Clinthorne et al. ............. 378/38 |
| 2006/0239400 | A1 | 10/2006 | Sukovic et al. ................. 378/38 |
| 2007/0140437 | A1 * | 6/2007 | Gotoh .......................... 378/197 |
| 2007/0262981 | A1 | 11/2007 | Hey et al. | |

FOREIGN PATENT DOCUMENTS

| | | |
|---|---|---|
| JP | H06-233752 | 8/1994 |
| JP | H10-243944 | 9/1998 |
| JP | 2000217808 | 8/2000 |
| JP | 2000262502 | 9/2000 |
| JP | 2003175027 | 6/2003 |
| JP | 2006239126 | 9/2006 |
| JP | 2007144136 | 6/2007 |

OTHER PUBLICATIONS

Office Action from the United States Patent and Trademark Office for U.S. Appl. No. 12/524,403 dated Apr. 13, 2012 (9 pages).
EP 09713389.6 Extended European Search Report and Opinion dated Dec. 23, 2010 (9 pages).
International Search Report for PCT/US2009/034750 dated Apr. 3, 2009 (2 pages).
Cranex Tome Product Information, Soredex, Archived web page from waybackmachine.com, Dec. 4, 2004.
Cranex Tome Imaging Principes, Soredex, Archived web page from waybackmachine.com, Dec. 10, 2004.
Cranex Tome New Features, Soredex, Archived web page from waybackmachine.com, Sep. 12, 2006.
Crabex Tome Brochure, Soredex, 2006.
Second Office Action from the State Intellectual Property Office of China for Application No. 2009801053143.5 dated Oct. 25, 2012 (English translation and original, 8 pages).
Office Action from the Intellectual Property Office of Japan for Application No. 2010547811 dated Mar. 11, 2013 (8 pages)
EP09713389.6 European Examination Report dated Mar. 22, 2013 (5 pages).
Office Action from the State Intellectual Proprty Office of the People's Republic of China for Application No. 200980105314.5 dated Apr. 18, 2013 (9 pages).

* cited by examiner

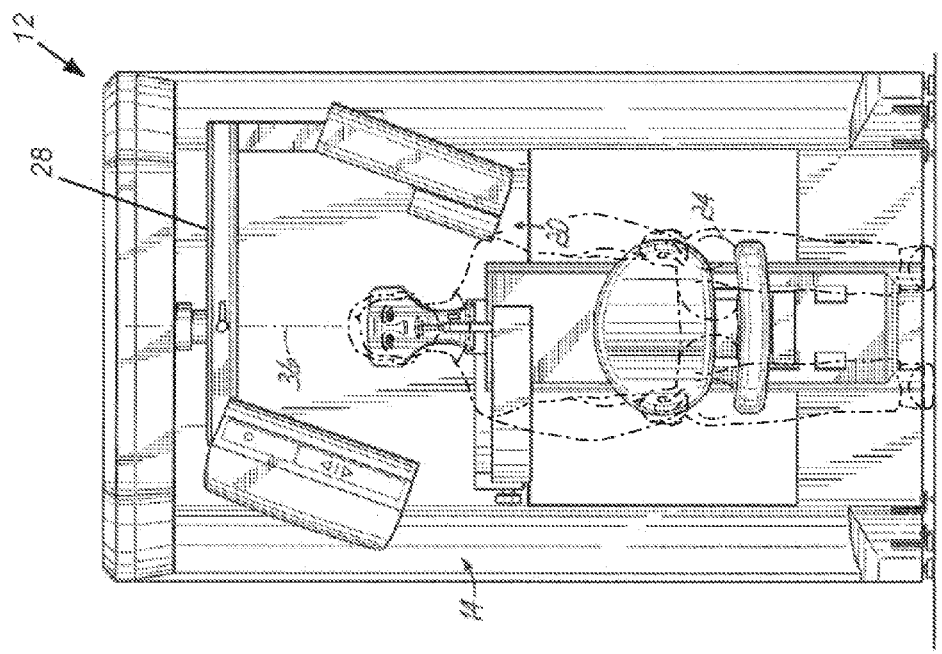
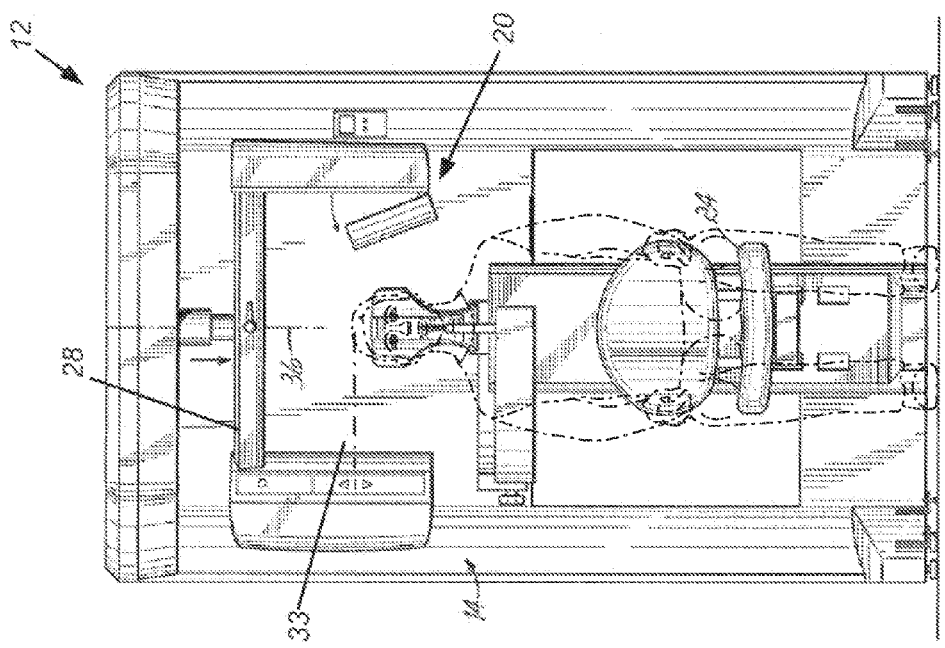

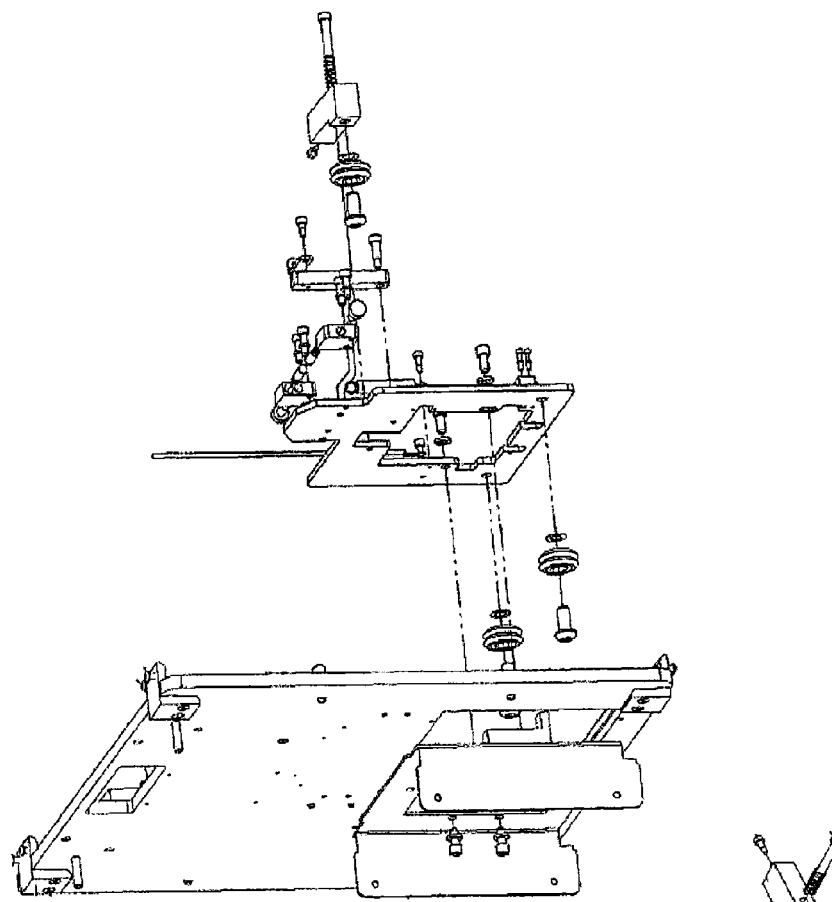
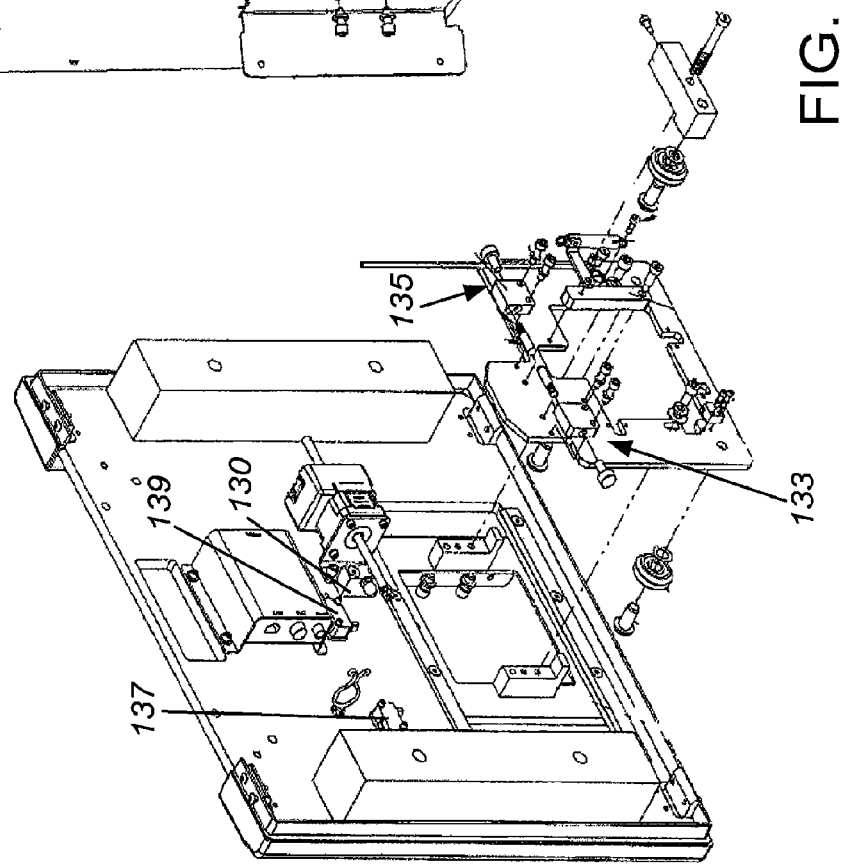
FIG. 13

ADJUSTABLE SCANNER

RELATED APPLICATIONS AND PRIORITY CLAIM

This patent application is a national stage filing under 35 U.S.C. 371 of International Application No. PCT/US2009/034750, filed Feb. 20, 2009, which claims the benefit of priority to U.S. Provisional Application No. 61/030,222, filed Feb. 20, 2008, the disclosures of which are incorporated by reference herein in their entireties. Priority to each application is hereby claimed.

STATEMENT OF INCORPORATION BY REFERENCE

This application incorporates by reference PCT application Ser. No. PCT/US08/51922 filed on Jan. 24, 2008 that claims priority to the U.S. provisional application 60/897,421 filed Jan. 24, 2007. This application also incorporates by reference the same US provisional application 60/897,421 filed Jan. 24, 2007.

TECHNICAL FIELD

The invention relates to the examination of objects with penetrating radiation, and especially to a scanner with a detector that can be positioned in different orientations to generate different images.

BACKGROUND

In a typical dental CT system, the patient sits upright, and the x-ray source and detector are mounted on opposite ends of a gantry that rotates about a vertical axis through the middle of the patient's head. In order to obtain sufficient data to cover the desired part of the head, which in CT imaging with high resolution is most of the extent of the skull in the horizontal plane, the detector must span a substantial distance in the circumferential direction perpendicular to the axis of rotation of the gantry, that is to say, the horizontal, direction.

Electronic detectors currently available include flat panel arrays of charge-coupled device (CCD) or other detectors, each of which converts incoming x-rays over a defined pixel area in a defined time to an electric charge that can easily be converted to a digital intensity value for subsequent computation. One flat panel detector commercially available from Varian Medical Systems, Inc., of Salt Lake City, Utah that is suitable for use in dental CT units has a pixel size of 127 μm (micrometers) square, and has an overall panel size of approximately 25 cm×20 cm. In dental imaging with a cone beam, because of the divergence of the beam towards the panel, that panel provides an effective Field of View approximately 16 cm×13 cm. When mounted with the long axis horizontal, the 25 cm length of the panel thus allows a Field of View with a diameter of approximately 16 cm, which is large enough to permit sufficient coverage of the imaged structures in the axial (horizontal) direction with high resolution for typical dental uses.

However, for most normal adults, the 20 cm height of the panel allows imaging only from the bottom of the lower jaw to about the bottoms of the orbits of the eyes (about 13 cm effective height at the level of the object being viewed). That is sufficient for most dental and oral surgery applications, but for some classes of orthodontic and orthognathic surgery applications an x-ray image up to the level of the glabella, roughly the level of the eyebrows, is essential. Such images, known as "full face" have in the past been produced by conducting two overlapping scans of 13 cm height at different levels and merging the images. Conducting two scans increases the radiation dose to the patient. Merging the images seamlessly is difficult, especially as the time taken to reposition the gantry, or the patient, between the two scans allows the patient to move. It would be possible to use a 25 cm square detector panel, which would have both the width to produce full coverage CT scans of the mouth diametrally, and the height to produce full-face scans in a single scan for about 98% of human adults, but the cost of detector panels increases disproportionately to the size of the panel, and could not easily be justified, when the full height is seldom required.

To improve the situation just described, the device described and illustrated in PCT application Ser. No. PCT/US08/51922 (which was filed on Jan. 24, 2008 claiming priority to U.S. Provisional Application 60/897,421 filed Jan. 24, 2007) was developed. Both of the application mentioned in the previous sentence are assigned to the owner of the current application, and incorporated by reference herein. Those applications disclose a device that rotates the detector (also known as a receptor) from a landscape to a portrait orientation, and vice versa. This rotation provides increased field of view when used in certain procedures. However, even with the rotation from landscape to portrait and vice versa, there are other field of view issues that can be addressed to provide better x-ray tomographic images and processes.

SUMMARY

For dental and facial imaging, a source of x-rays or other penetrating radiation and a detector are mounted opposite one another on a rotatable gantry, so that the head of the patient can be positioned between the source and the detector, with the axis of rotation of the gantry passing through the patient's head. The detector or the source are mounted so they can translate and/or pivot horizontally or vertically. The gantry is angulated so that the source or the detector may not be at the same height relative to the patient's head. The gantry can telescope, moving the source and the detector closer together or further apart. The collimator changes dynamically with the motion of the gantry and/or the source and detector to scan a smaller portion of the scan field.

The invention also provides data produced by the methods and systems of the invention In one embodiment, the invention provides an apparatus for dental and facial imaging. The apparatus includes a controller; a rotatable gantry; and a source of penetrating radiation mounted on the gantry. The source of penetrating radiation includes a beam limiter with a plurality of doors. The apparatus also includes a detector of penetrating radiation mounted opposite the source on the gantry, so that the head of a patient can be positioned between the source and the detector, with the axis of rotation of the gantry passing through the patient's head. The detector is mounted translatably on the gantry between a first position and a second position and includes a first stop positioned at the first position and a second stop positioned at the second position. Movement of the detector between the first position and the second position is controlled so that the movement of the detector is slowed in a first direction before the detector reaches the first stop and movement of the detector is slowed in a second direction before the detector reaches the second stop. The controller is configured to coordinate movement of the rotatable gantry, the plurality of doors of the beam limiter, and movement of the detector.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings:

FIG. 7 is an embodiment, having a detector that rotates about an axis as shown and provides for tilt of the detector around its u axis.

FIG. 8 is an embodiment having a source and a detector on the gantry in an angled manner, and at different heights relative to the object being scanned.

FIG. 13 is an exploded view of the detector illustrating components that are used to translate the detector array.

DETAILED DESCRIPTION

Reference will now be made in detail to various embodiments of the present invention, examples of which are illustrated in the accompanying drawings.

Figure 1:
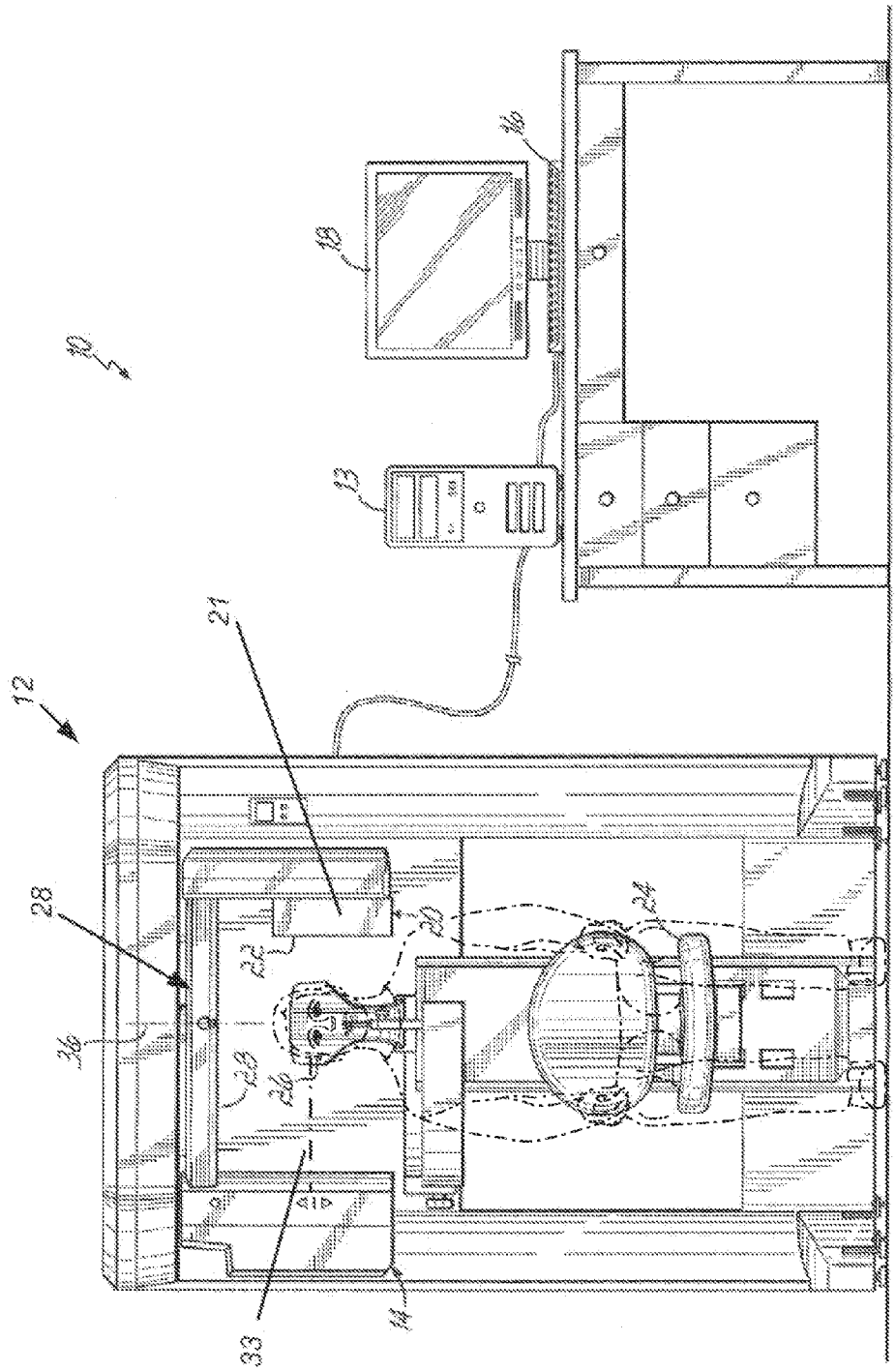
FIG. 1 is a schematic view of apparatus for generating a tomographic image.

Referring to the drawings, FIG. 1 shows a tomographic apparatus 10 according to an embodiment of the invention, which includes a scanner 12 and a computer 13 controlled by a console 16 with a display 18. The scanner 12 includes a source of x-rays 14, an x-ray detector 20 including a movable housing 21 (e.g., a plastic housing) supporting a rectangular sensor array 22. The scanner 12 also includes a support 24 for an object to be imaged. In an embodiment, the scanner 12 is arranged to image the head, or part of the head, of a human patient (not shown), especially the jaws and teeth. The support 24 may then be a seat or chair with a rest or restrainer 26 for the head or face (not shown) of the patient. The x-ray source 14 and x-ray detector 20 are then mounted on a rotating carrier or gantry 28 so as to circle round the position of the patient's head, while remaining aligned with one another. The x-ray detector 20 includes a panel having a rectangular array of x-ray sensitive elements. The x-ray detector 20 records a stream of x-ray shadowgrams of the patient's head from different angles. The computer 13 receives the x-ray image data from the scanner 12, and calculates a 3-dimensional spatial distribution of x-ray density.

The imaging of the patient's head and calculation of the spatial distribution may be carried out by methods and apparatus already known in the art and, in the interests of conciseness, are not further described here. Suitable apparatus is available commercially, for example, the i-CAT Cone Beam 3-D Dental Imaging System from Imaging Sciences International of Hatfield, Pa.

A first embodiment of the invention is now described referring to FIGS. 1-6. The x-ray detector 20 is supported by a cylindrical roller bearing 30 on a mounting panel 32 (shown in FIG. 2 and discussed in documents incorporated by reference) attached to the gantry 28. Not shown are electrical cables and a guard that protects the cables from the moving parts. The x-ray source 14 is arranged to emit a beam of x-rays along an axis (the "x-ray axis" 33) that is aligned with the center of the x-ray source 14, and intersects perpendicularly the gantry axis of rotation 36 of the gantry 28 relative to the frame of the scanner 12.

Figure 2:
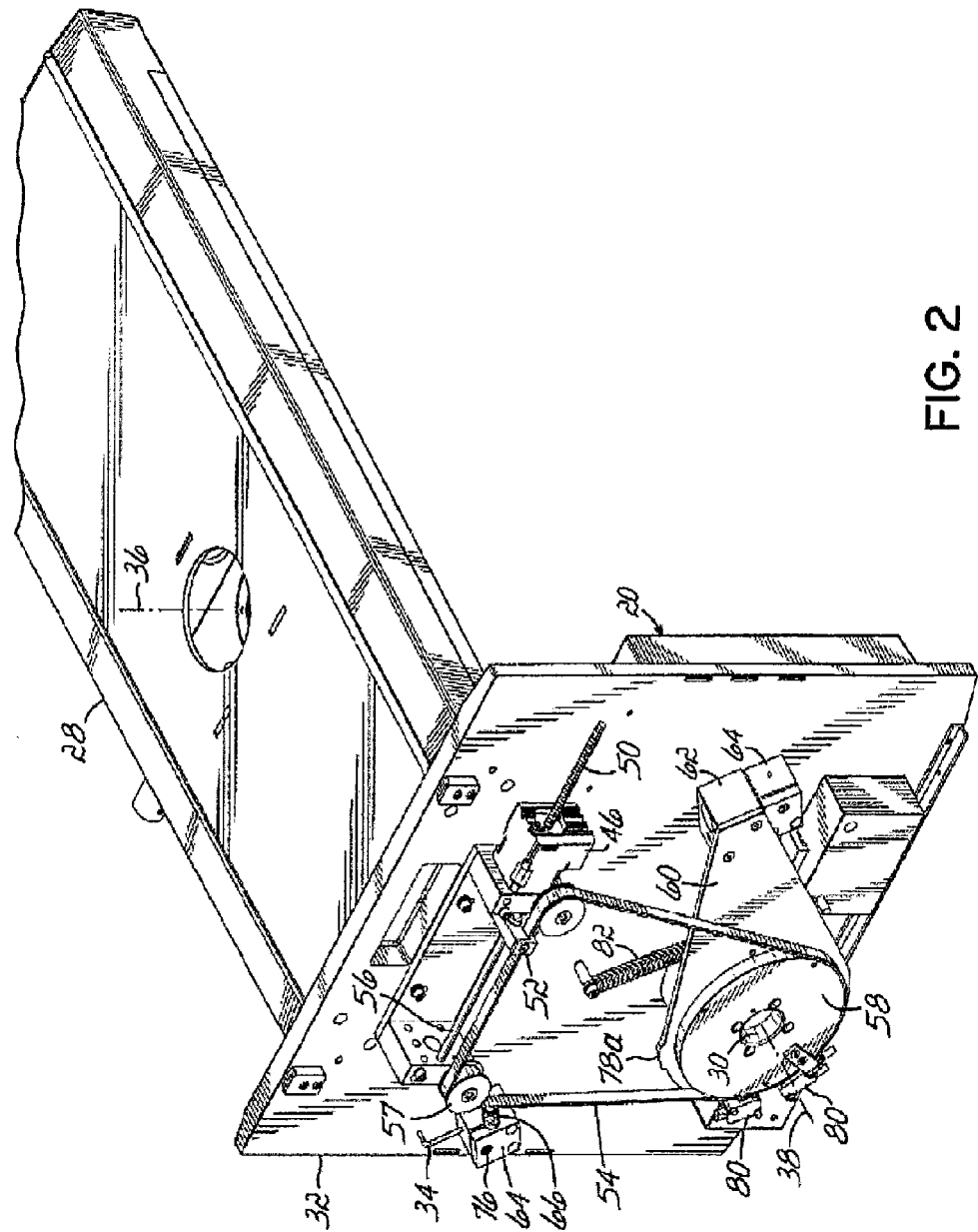
FIG. 2 is a perspective view of part of a gantry of the apparatus of FIG. 1, with a cover removed to show a mechanism to rotate the detector panel.
Figure 3:
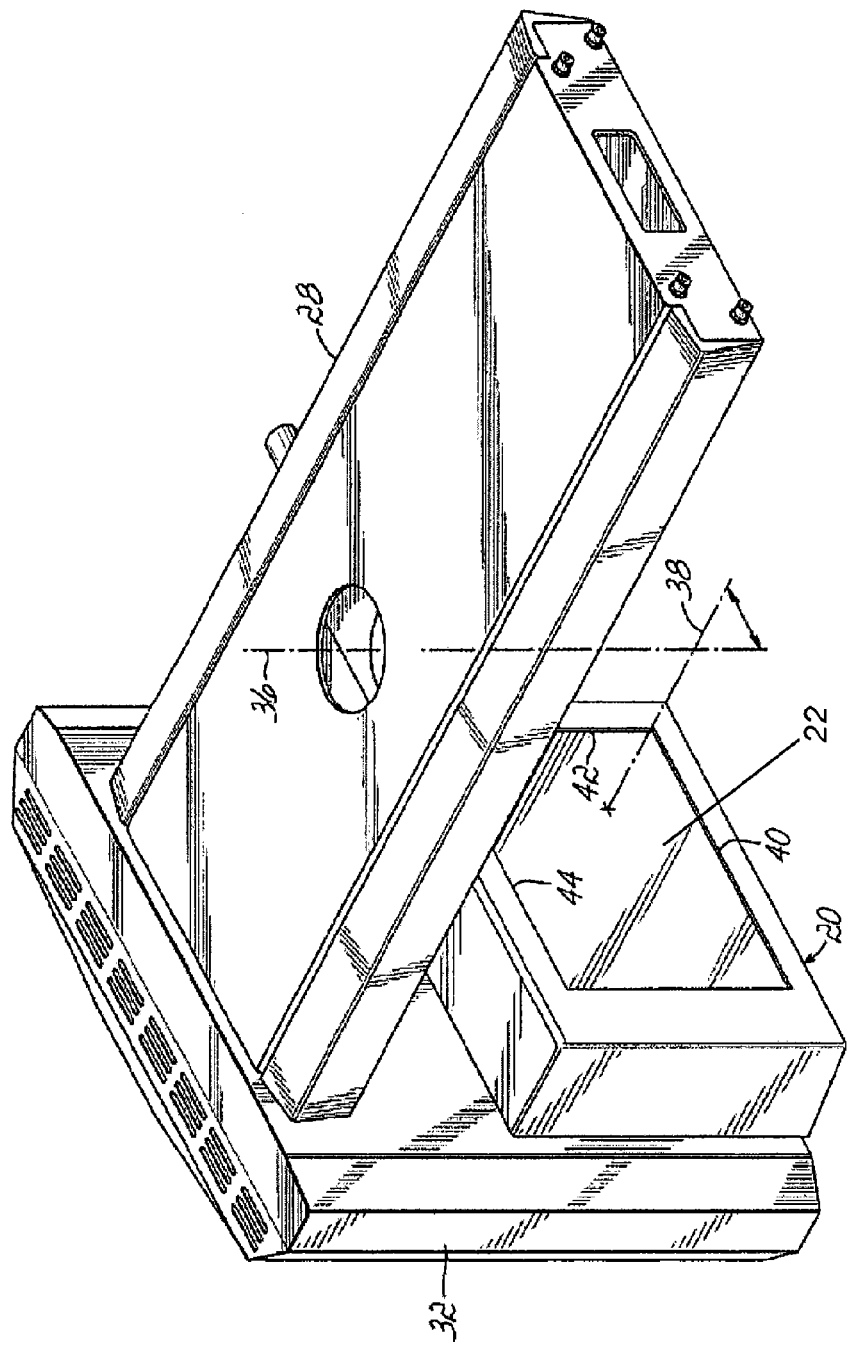
FIG. 3 is a different perspective view of the same part of a gantry as in FIG. 2.
Figure 5A:
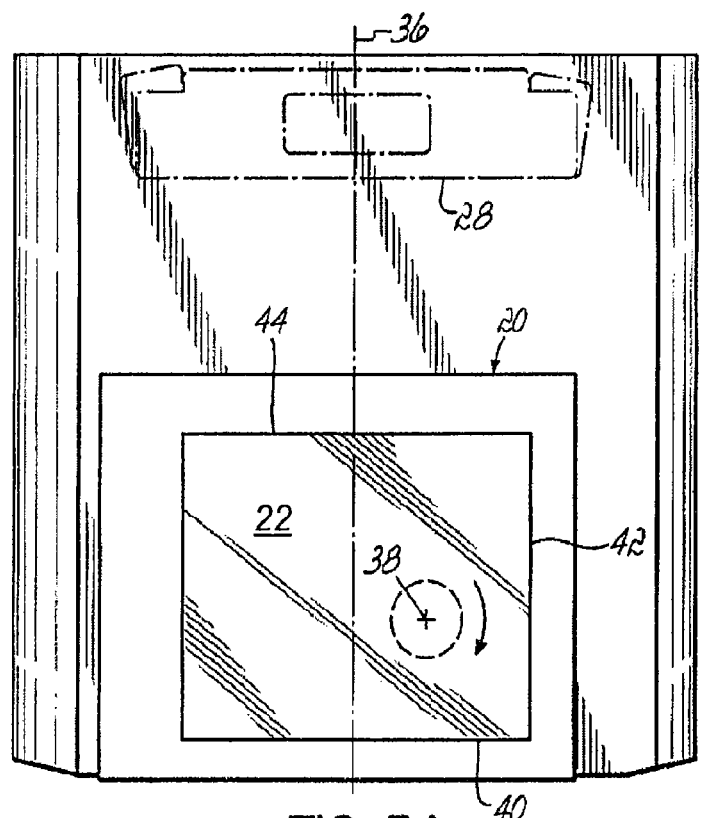
FIG. 5A is an elevational view of the interior side of the detector end of FIG. 2 in a landscape orientation.
Figure 5B:
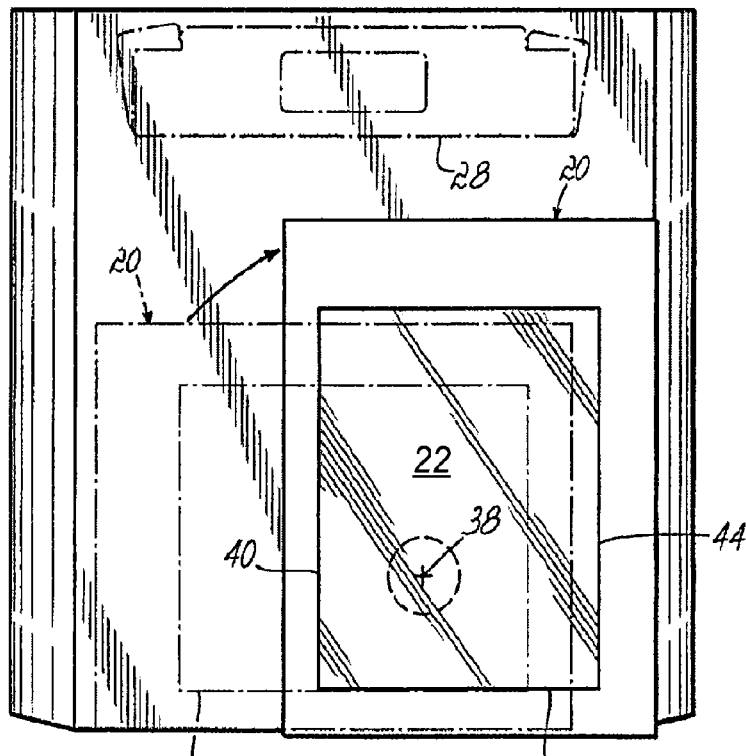
FIG. 5B is an elevational view of the interior side of the detector end of FIG. 2 in a portrait orientation.

The detector axis 38 (FIGS. 3, 5A, and 5B) is offset horizontally from the x-ray axis 33, and is positioned equal distances from the bottom, and one end of the rectangular sensor array 22. For an example using numbers, in one embodiment, the panel has a rectangular sensor array 22 with an operative area 20 cm by 25 cm, and the detector axis 38 is then 10 cm from each of the bottom edge 40 and one short edge 42 (the left end as seen in FIG. 2 or the right end as seen in FIGS. 3, 5A, and 5B) of the sensor array 22. Then, when the x-ray detector 20 is rotated 90° about the detector axis 38 from the landscape orientation seen in FIG. 5A to a portrait orientation FIG. 5B, the detector assumes a position where a bottom short edge 42 in portrait orientation is on the same line as the bottom long edge 40 in landscape orientation.

An additional embodiment also contemplated, but not shown, is as follows. The detector axis 38 is offset horizontally from the x-ray axis 33, and is positioned equal distances from the top edge 44, bottom edge 40, and short edge 42 of the rectangular sensor array 22. For an example, using the same numbers as in the embodiment shown, the panel has a rectangular sensor array 22 with an operative area 20 cm by 25 cm, and the detector axis 38 is then 10 cm from each of the top, bottom, and one end (the left end as seen in FIG. 2) of the array. Then, when the x-ray detector 20 is rotated 90° about the detector axis 38 from the landscape orientation a portrait orientation, the detector assumes a position (not shown) where the left-hand long edge in portrait orientation is on the same line as the left-hand short edge in landscape orientation, and the bottom long edge in portrait orientation is on the same line as the left-hand short edge in landscape orientation.

The roller bearing 30 is a large-diameter bearing, for example, 5.5 cm diameter, with minimal play and backlash. A high-resolution imaging panel of the x-ray detector 20 may have a pixel size of, for example, 127 µm. The positioning of the x-ray detector 20 should be stable, both within a scan and between scans, to within a fraction of a pixel, say, 0.1 mm (100 µm), for high-quality imaging without extra computation. A very stable bearing 30 is therefore desirable.

Apart from its mounting, the x-ray detector 20 may be a commercially available flat-panel x-ray detector, such as those supplied by Varian Medical Systems, Inc., of Salt Lake City, Utah.

Figure 4A:
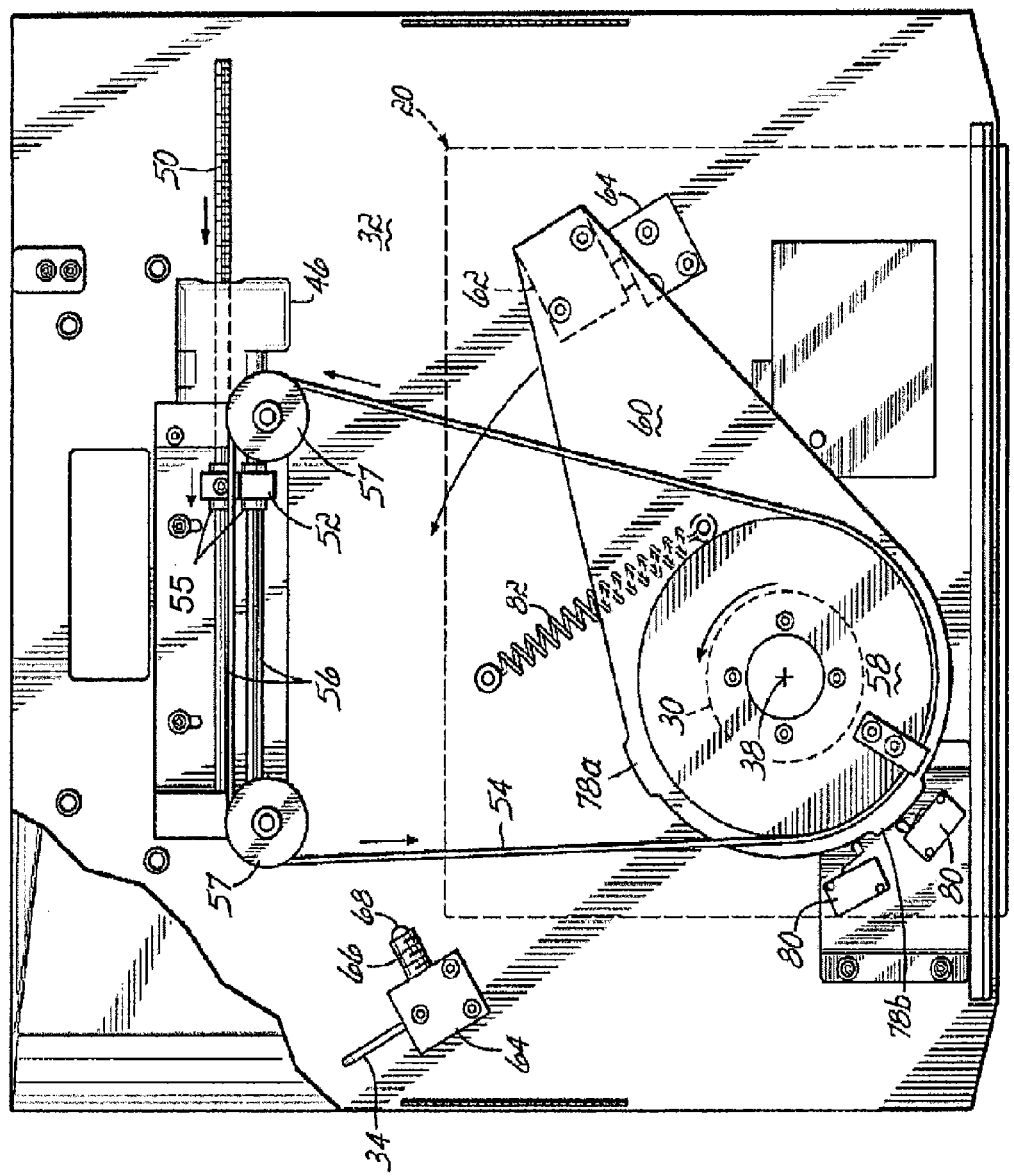
FIG. 4A is an elevational view of the outside of the detector end of FIG. 2 with the cover and a cable guard removed, where the detector is in a landscape orientation.
Figure 4B:
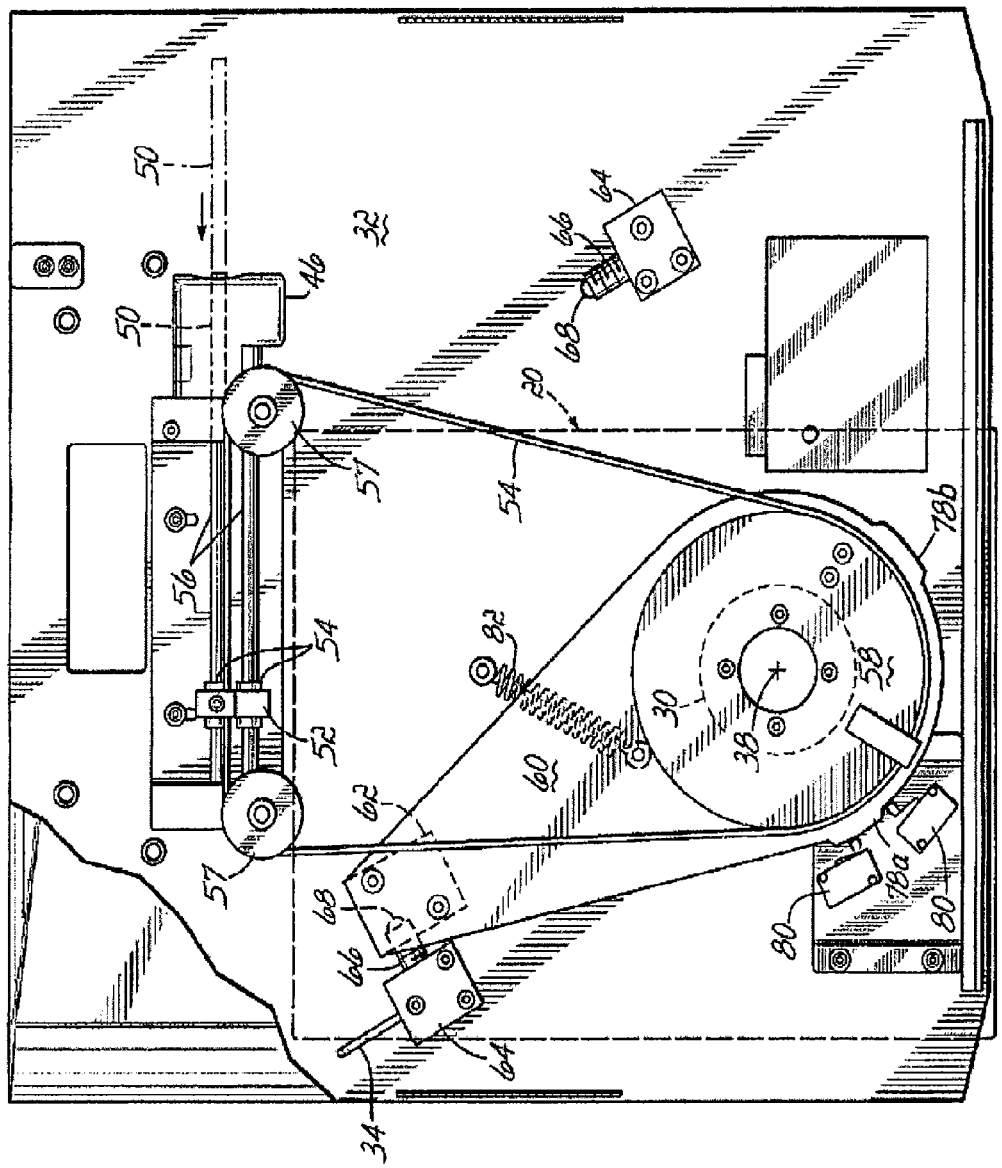
FIG. 4B is an elevational view of the outside of the detector end of FIG. 2 with the cover and a cable guard removed, where the detector is in a portrait orientation.

The position of the x-ray detector 20 is controlled by components visible in FIGS. 2, 4A, and 4B. A stepper motor 46 having an armature 48 (not shown) with internal threads extends and retracts an externally threaded shaft 50. The shaft is connected to a grab block 52 that has guides 55 that travel along two fixed rods 56 that resist the rotational forces of the motor. The grab block 52 is clamped to a belt 54. The belt passes over two pulleys 57, and around a journal 58 that is attached to the roller bearing 30. As the motor 46 extends and retracts the shaft 50, the belt 54 moves clockwise and counterclockwise to rotate the journal 58 and, thereby, the x-ray detector 20.

Figure 6:
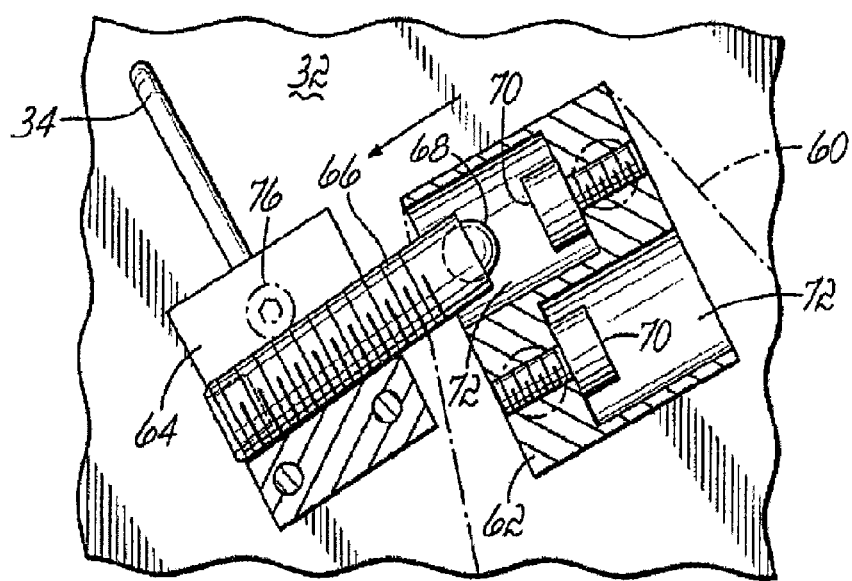
FIG. 6 is a detail view of a portion of the embodiment of FIG. 2.

Attached to the journal 58 is an arm 60 carrying a head 62. As the journal 58 rotates, the head 62 moves along an arc between two end stops 64 positioned so that the journal 58 and the arm 60 can rotate exactly ninety degrees between the end stops 64. The end stops 64 are provided with pins 66 for precise adjustment of the positions at which the head 62 is stopped by the end stops 64. The stops have hardened contact surfaces 68 and the head has hardened contact surfaces 70 (FIG. 6). The hardened surfaces are located within counterbores 72 in the head so that both hardened surfaces are along a single plane extending from the detector axis 38. The non-contact end of the pins 66 rest against an adjustment screw 74 (not shown) within the end stop 64. The stop is split, so that tightening of a screw 76 clamps down on the pin 66.

To maintain precision it is important that the contacts do not wear or deform. A slow, low-power rotational speed prior to contact between the arms and the stops lessens impact. To this end, the journal 58 is provided with protrusions or lobes 78a and 78b that act as actuators for a pair of limit switches 80 that detect when the journal 58 is near one of its end positions. The limit switches signal the position to the computer 13 for adjusting the speed of the motor. The grab block 52 continues to move at a speed dependent on the position of the journal 58 and comes to a stop when the contact 70 in the head 62 comes into contact with the contact 68. A spring 82 is pivotally connected to the mounting panel 32 and the journal 58 to assist the motor and help prevent stalling of the motor during operation thereof.

The control of the position described above is just one way contemplated for low-speed contact. Alternatively, the movement of the journal 58 may be tracked in another way. For example, the lobes 78a, 78b and limit switches 80 may have secondary contacts arranged to signal to the computer 13 when the head 62 is a short distance from one of the end stops 64.

In operation, the pins 66 are set so that the end positions of the x-ray detector 20 are landscape and portrait positions with the rectangular array aligned with the gantry axis 36. The alignment may be precise to within a fraction of the size of a pixel over the length of the array, although the amount of precision required may be different for different embodiments of the invention. The computer 13 may be programmed to rotate the journal 58, and thus the x-ray detector 20, at a moderate speed, taking several seconds for a ninety degree rotation. Then, just before the head 62 reaches the end stop 64 at the far end of the rotation, the motor 46 is braked, and the head 62 closes gently against the pin 66, so that the x-ray detector 20 is accurately positioned without an impact that might damage any part of the system. In particular, it is desirable to avoid, as far as practical, deformation of the head 62 or the pins 66 that might result in the end position of the x-ray detector 20 drifting.

In use, the scanner 12 may be used with the x-ray detector 20 in landscape orientation for a computed tomography scan of the mouth region. A rectangular sensor array 22 that is 25 cm wide allows the detection of x-rays sufficiently far from the axis to allow for computed tomography of a quality sufficient for almost all dental and oral surgery. A rectangular sensor array 22 that is 20 cm high allows most human heads to be imaged over a region extending from just below the lower jaw to about the bottom of the eye-socket. If only a region of lesser height needs to be imaged for a specific purpose, the height of the x-ray beam can be reduced by an adjustable collimator to reduce the x-ray dose to the patient. A collimator with four independently controllable jaws is suitable, and in some jurisdictions is required, in order to collimate the x-ray beam to the changes in the position of the detector panel. Such collimators are well-known in the art and, in the interests of conciseness, are not further described here.

With the x-ray detector 20 in portrait orientation, a rectangular sensor array 22 that is 25 cm high allows most human heads to be imaged over a region extending from just below the lower jaw to about the level of the glabella, roughly eyebrow level. The extra height is required for certain types of orthodontic and orthognathic surgery, and a 25 cm high rectangular sensor array 22 is then sufficient for about 98% of human adults. The positioning of the detector axis 38 relative to the x-ray detector 20 results in the bottom of the rectangular sensor array 22 of the detector panel being at the same level in both portrait and landscape orientations, so that the positioning of the patient in the scanner 12 is identical in both portrait and landscape scanning, which reduces the risk that a scan has to be repeated because the patient was incorrectly positioned.

With a 20 cm by 25 cm rectangular sensor array 22 in portrait orientation, there is some loss of image quality, because of the reduced width of the detector. However, the positioning of the detector axis 38 relative to the x-ray detector 20 may be chosen so that one side of the rectangular sensor array 22 is the full 12.5 cm from the x-ray axis, with the other side of the array only 7.5 cm from the x-ray axis. The 12.5 cm extent on one side of the axis gives better coverage diametrally in computed tomography imaging than a panel extending to 10 cm on both sides of the x-ray axis, by using a known reconstruction method commonly referred to as "half-beam mode." Although the image quality is less than with a 25 cm wide array, it has been found to be sufficient for most forms of orthodontic and orthognathic surgery. Where a high resolution image of the actual teeth is required, for example, for some forms of oral diagnosis or surgery, the 25 cm high full face scan can be combined with a second scan, using the x-ray detector 20 in 25 cm wide landscape orientation, but with the x-ray beam collimated to only 6 or 8 cm high. Such a double scan can be conducted with less x-ray dosage to the patient than would result from a full-face scan using two overlapping scans from a scanner with a fixed detector panel 25 cm wide by 20 cm high.

Figure 10:
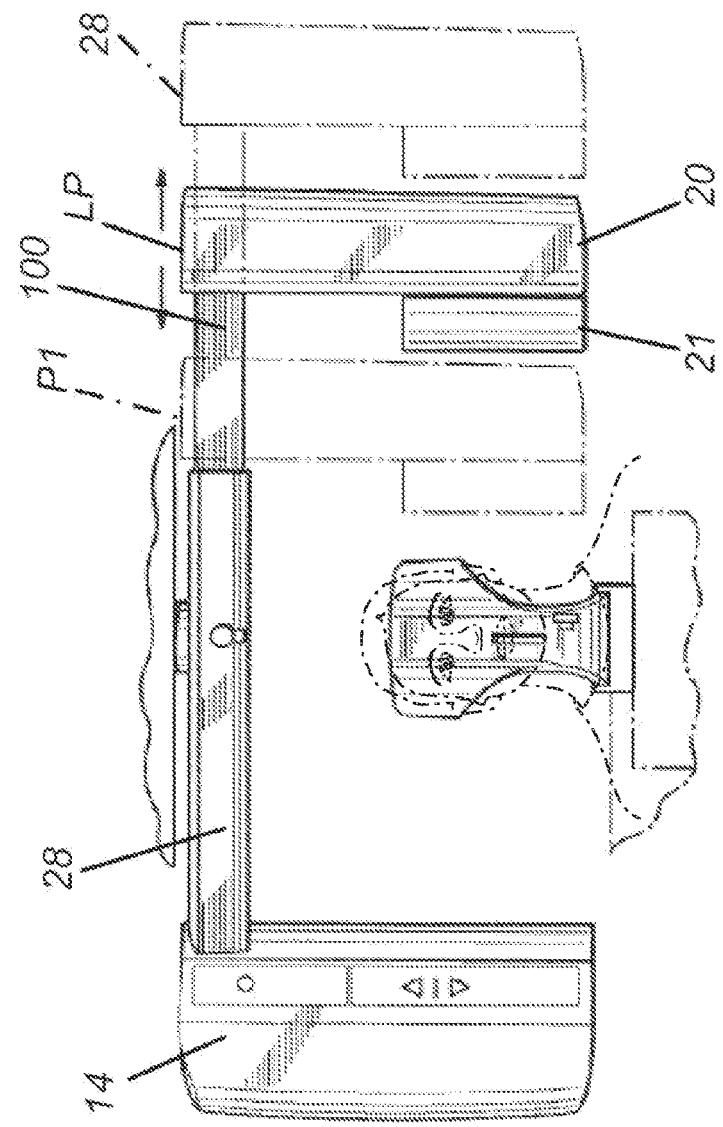
FIG. 10 illustrates an embodiment in which the gantry telescopes.
Figure 11:
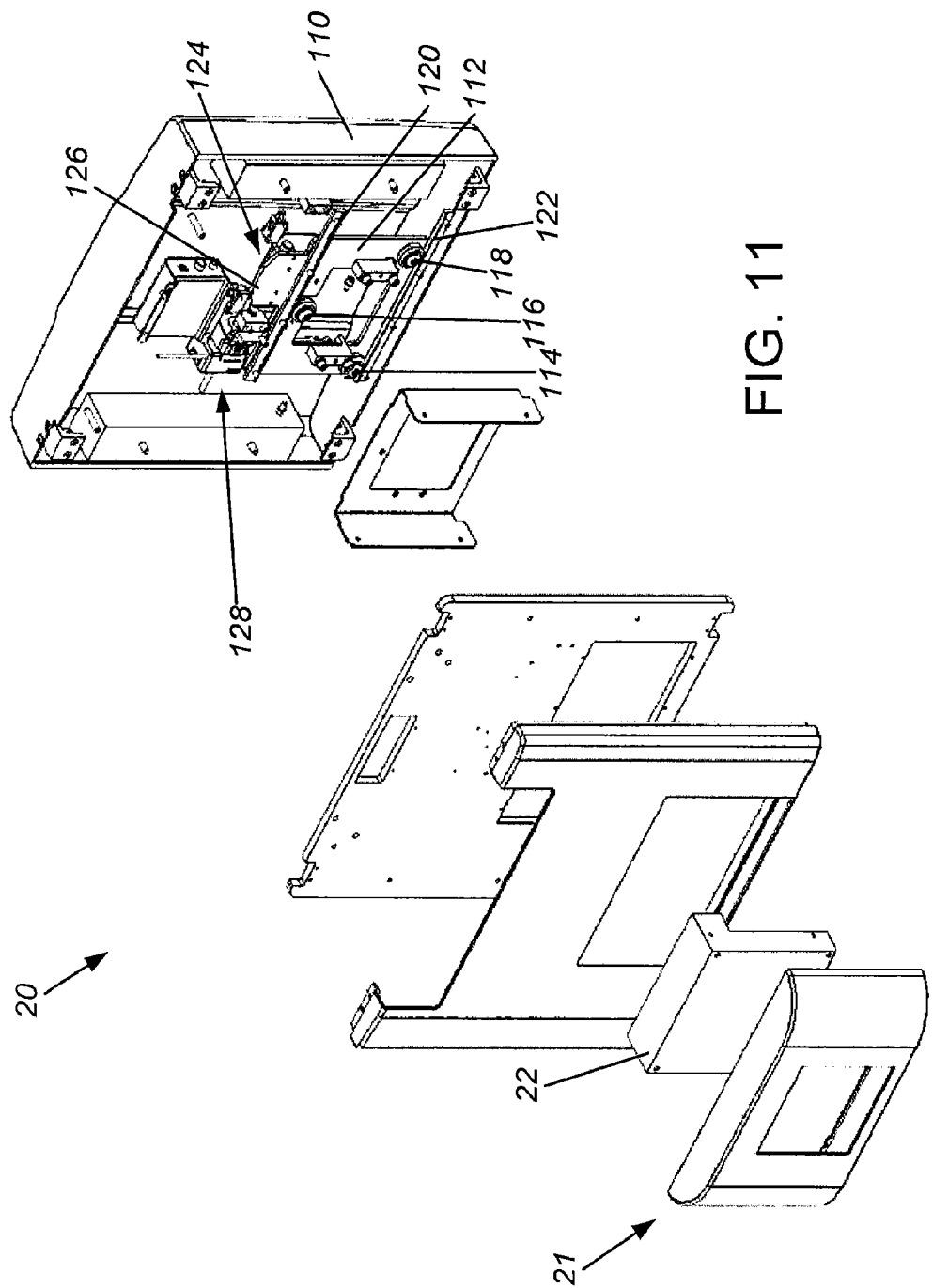
FIG. 11 illustrates an embodiment in which the detector array translates.
Figure 12:
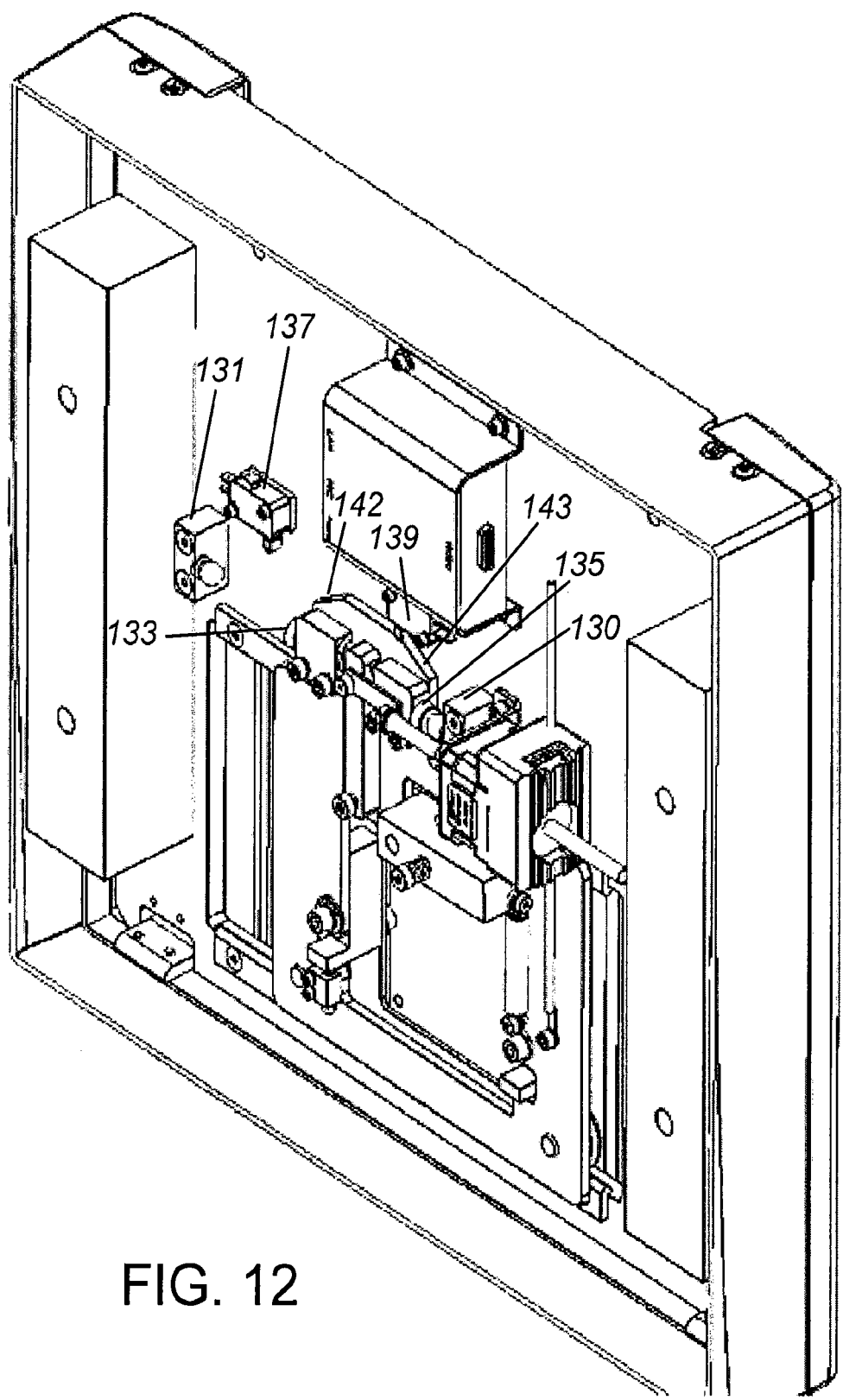
FIG. 12 illustrates components of the detector which are used to translate the detector array.

In addition to changing the orientation of the sensor array 22 from a landscape orientation (FIG. 5A) to a portrait orientation (FIG. 5B) it is possible to change orientation of the sensor array 22 with respect to the x-ray axis such that the x-ray axis intersects the front surface of the sensor array at a non-right angle. As noted above, the x-ray axis 33 intersects the gantry axis 36 perpendicularly, and normally, the sensor array is aligned so that x-ray axis 33 intersects the front surface of the sensor array 22 perpendicularly. In the embodiment shown in FIG. 7, the sensor array 22 is pivotally mounted to the x-ray detector 20 so that it can be moved along an arc 91 such that the x-ray axis 33 intersects the sensor array 22 at an angle 92 that is less than 90°. Changing the orientation of the sensor array 22 changes the focus of the x-rays and, therefore, the particular location of the subject that is imaged by the apparatus 10. FIG. 10 illustrates an embodiment where the gantry 28 has a telescoping arm 100. The telescoping arm 100 is movable along a linear path LP between a first position P1 and a second position P2. By changing the position of the arm 100 along the path LP the focus of the x-rays emitted from the source 14 may be changed. As the gantry expands or contracts in length, the relative positions of the source, the object, and the detector are varied. This results in variations in scan quality, field of view, and resolution.

Specifically, when the distance between the detector and patient/object is increased, there is greater magnification, and greater resolution. However, there is a narrower field of view and the resolution gain will at some point be offset by blurring in the edges of the images as a result of focal spot effects, which are caused by the fact that the x-ray source is not a point source, but rather has a finite diameter such as 1 millimeter. Decreasing the distance between the detector and patient/object increases field of view, and reduces focal spot effects thereby improving the sharpness of edges. However, these features come at the expense of reduced magnification, and reduced resolution. A telescoping feature of the gantry permits selection of a desired combination of magnification, field of view, and control of focal spot effects for a given application.

An additional embodiment is shown in FIG. 8, in which the source of x-rays 14 and the x-ray detector 20 are pivotable such that the angle at which the x-ray-axis 33 intersects a patient or subject is variable. The embodiment shown in FIG. 8 permits imaging of a subject from different angles without requiring the subject to move. This variability may lead to better or enhanced images of particular locations of interest on the subject. For example, certain defects or abnormalities might be visible or detectable only when imaged from a particular orientation or point of view. The enhanced images may facilitate diagnosis and treatment.

Other additional alternative embodiments for movement of the detector panel or source in a rotatable gantry CT imaging system, that may substitute or complement the rotational movement described above are discussed below. In the description provided, reference is made to three directional axes. These axes apply to both of the source and the detector. They are the u, v, and w axes and are shown in the FIG. 9. X, y, and z axes labels are intentionally not used, because they may be confused with the x, y, and z directions of the scan field volume data.

Initially, some discussion of the factors involved in scanning is required. The "ray point" is defined as the location on the detector panel at which a perpendicular ray leaving the point source hits the detector panel. The location of this ray point to the u axis of the detector is a strong parameter, that is, the quality of reconstruction is a strong function of the relative positioning of the ray point on the u axis. To the v axis, the ray point location is an important parameter but is less strong of a parameter as the location to the u axis. These two ray point location parameters are tied to the registration and calibration of the translating detector. Each of the embodiments presented herein provides for registration and calibration of the detector in a manner that can improve the parameters affecting image quality.

Figure 9:
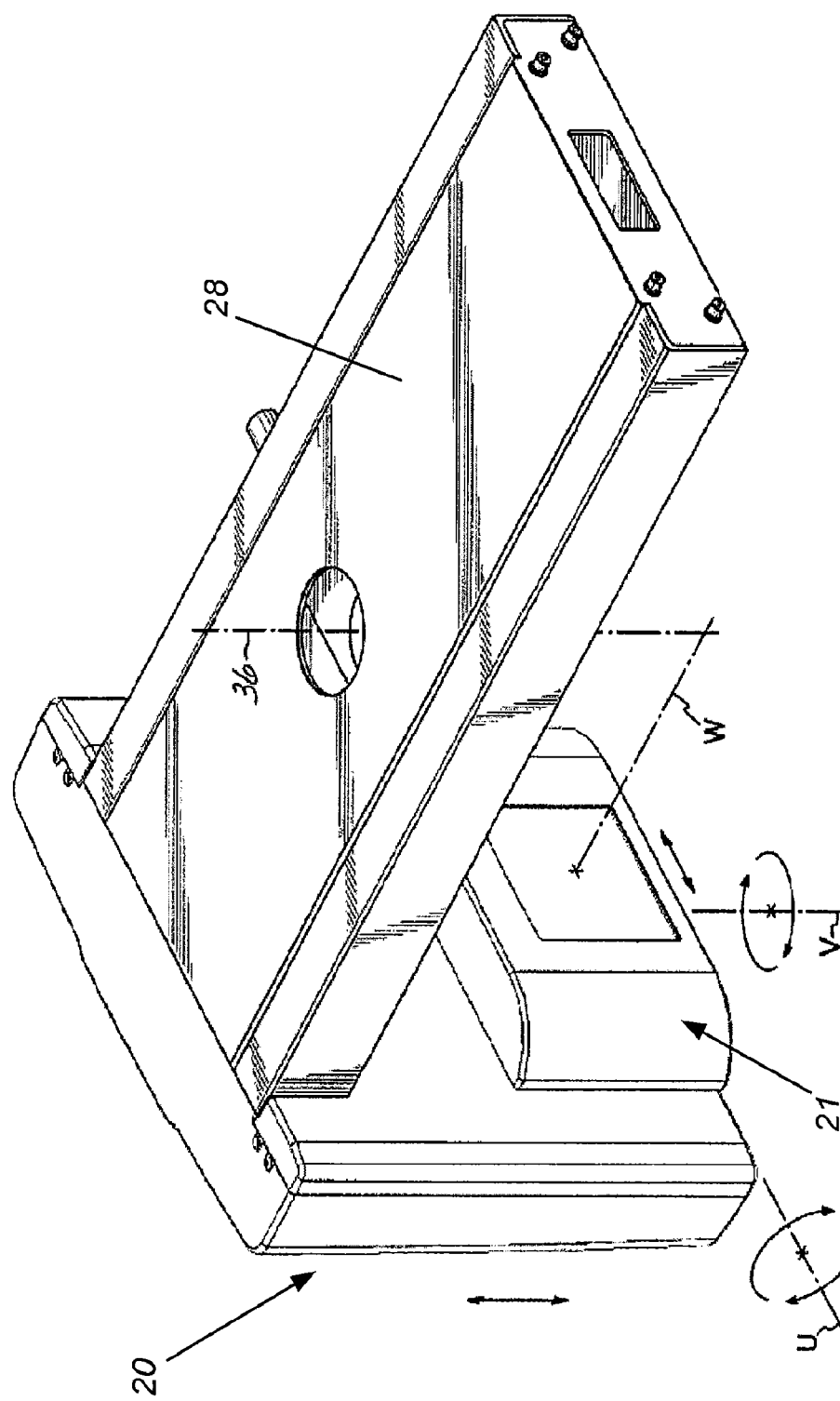
FIG. 9 illustrates u, v, and w axes used to describe motion of a detector panel and source in a rotatable gantry imaging system.

In a first alternative embodiment, detailed in FIGS. 11 through 18 herein, the detector translates (moves) along the u axis as illustrated in FIG. 9. This linear shift occurs without any movement to the source and center of rotation. This introduces a large amount of shift (in the u direction) to the vertical rays incident on the detector, and typically would be used when the machine operates in half-beam mode. The result is a larger field of view without increasing detector size. A similar result may be obtained by rotating the detector from a portrait to a landscape mode as described above and in PCT application Ser. No. PCT/US08/51922 filed on Jan. 24, 2008. The difference with the present embodiment is that it shifts the panel rather than rotates it. The same registration is required as the case of the rotating detector since there needs to be precise relationship between the location of the detector and the gantry.

In the illustrated embodiment, the x-ray detector 20 includes detector panel or housing 110 and a detector support (or guide plate) 112 having three guide wheels 114, 116, and 118 that run along two guide rails 120 and 122. The detector support 112 has a drive connector 124 connecting it to a drive shaft or a drive screw 126 and a stepper motor 128. Powering the motor in one direction or the other translates the detector support 112 and thereby the sensor array 22. It is important that the sensor array be precisely registered. There are rigid stops 130 and 131 (FIG. 14) with hardened contacts mounted on the on the housing 110. On the detector support 112 there are also rigid stops 133 and 135 with hardened contact surfaces. In alternate constructions, the stops may be adjusted by threading a backing screw into and out of the rigid stops and then locking them in place. To maintain precision it is important that the contacts do not wear or deform. To this end, the housing has two limit switches 137 and 139 and the detector support 112 has two trigger surfaces 142 and 143 for those limit switches. When the detector support contacts a limit switch, a set number of steps is sent to the motor to drive rigid stops 133 and 135 to a position near or adjacent to rigid stops 130 and 131. However, in alternate constructions is may be desirable to drive the motor at variable speeds. For example, it may be desirable that the detector translates quickly such that most of the translation may be done quickly, but a slowed and lower power speed is instituted to the motor prior to contact between the rigid stops to lessen their impact.

In a second alternative embodiment, the detector translates (moves) along the v axis. This may be accomplished by configuring the detector panel translating components, described previously, in positions rotated approximately 90 degrees. While translating the detector panel vertically may not increase field of view, it allows shaping of volume coverage. For example, the top of the scan area naturally exhibits a cone shape simply because of the direction of the cones. By shifting the detector in the v-direction this shape may be modified to increase/reduce the amount of cone or in some cases invert the cone.

Although the figures show an embodiment in which the detector translates on the detector pod, while the connection between the horizontal beam member of the gantry and the detector pod remains fixed, it would also be possible to make the pod movable relative to the base in translation and/or rotation. The following discussion relates to other such embodiments.

In a third and fourth alternative embodiments implementing principles of the present invention, the detector may be rotated about its u or v axis respectively. Rotation about the w axis is generally disclosed in the above-referenced patent application. Rotation about the u or v axes may increase the effective resolution and/or achieve a higher resolved volumetric scan.

In a fifth and sixth alternative embodiment, translation along axis u or v may be done to the source, as was done in alternate embodiments 1 and 2, respectively, for the detector.

In a seventh and eighth alternative embodiment, the same rotation about axis u or v may be done to the source, as was done in alternate embodiments 3 and 4, respectively, for the detector. Rotation of the source about the w axis (the axis through which x-ray is delivered from the source) is unlikely to have great effect on the image for the reason that the source is (nearly) a point source.

In a ninth alternative embodiment, the gantry may be angulated (refer to FIG. 8 as an example) so that the source and detector may be rotated along its u axis. An example of an application of this concept is to place the x-ray source 14 in a relatively low position, preferably below the shoulders of the subject, and point the source 14 upward. This may be accomplished in a number of ways including mounting the source on tracks or guides such that the source 14 is moveable along a vertical axis with respect to the end of the gantry 28. When the source 14 is lower, the detector is, in relative terms, higher up. An angulated orientation may be static, or may be selected dynamically for a particular scan operation, using fixtures in the gantry that orients it in a controllable manner. As noted above, the embodiment shown in FIG. 8 permits imaging of a subject from different angles without requiring the subject to move. This variability may lead to better or enhanced images of particular locations of interest.

In a tenth alternative embodiment, dynamic beam limitation (sometimes referred to as dynamic collimation) of the x-ray to targets only one specific region of the scan field. In this embodiment, the machine rotates around the scan field in the same manner as if the whole field of view is considered. However, a beam limiter is used to trim the x-ray beam dynamically, so that the x-ray field covers only that volume that is of interest.

In this tenth alternative embodiment, in some cases, the beam limiter may need to create a moving field in order to maintain illumination of the volume of interest as the gantry rotates. This requires the use of a dynamic beam limiter, programmably controlled to change the illuminated area as the machine rotates around the scan field.

Figure 14:
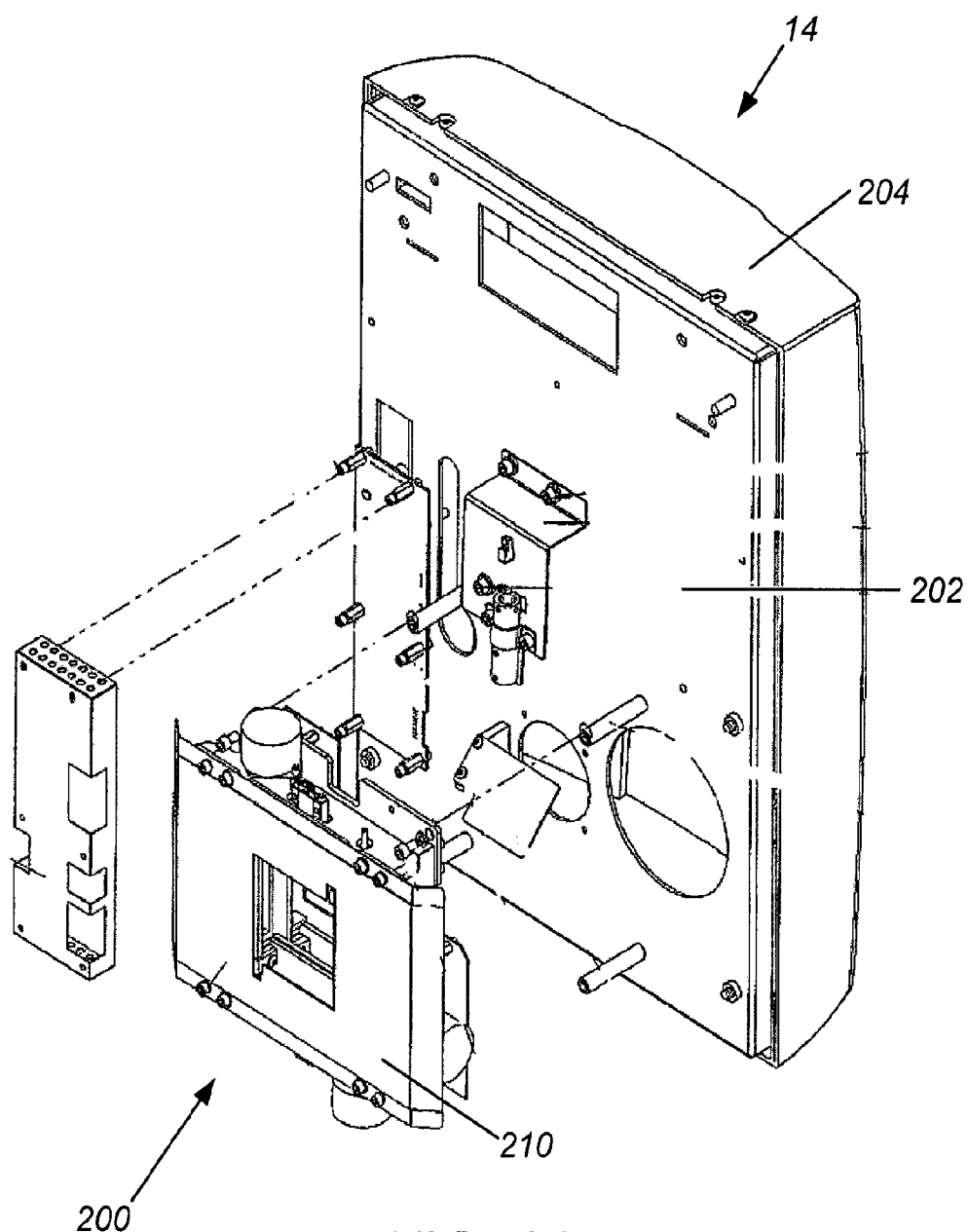
FIG. 14 is a partially exploded view of an x-ray source illustrating components of a beam limiter (or components that are used to collimate x-rays).
Figure 15:
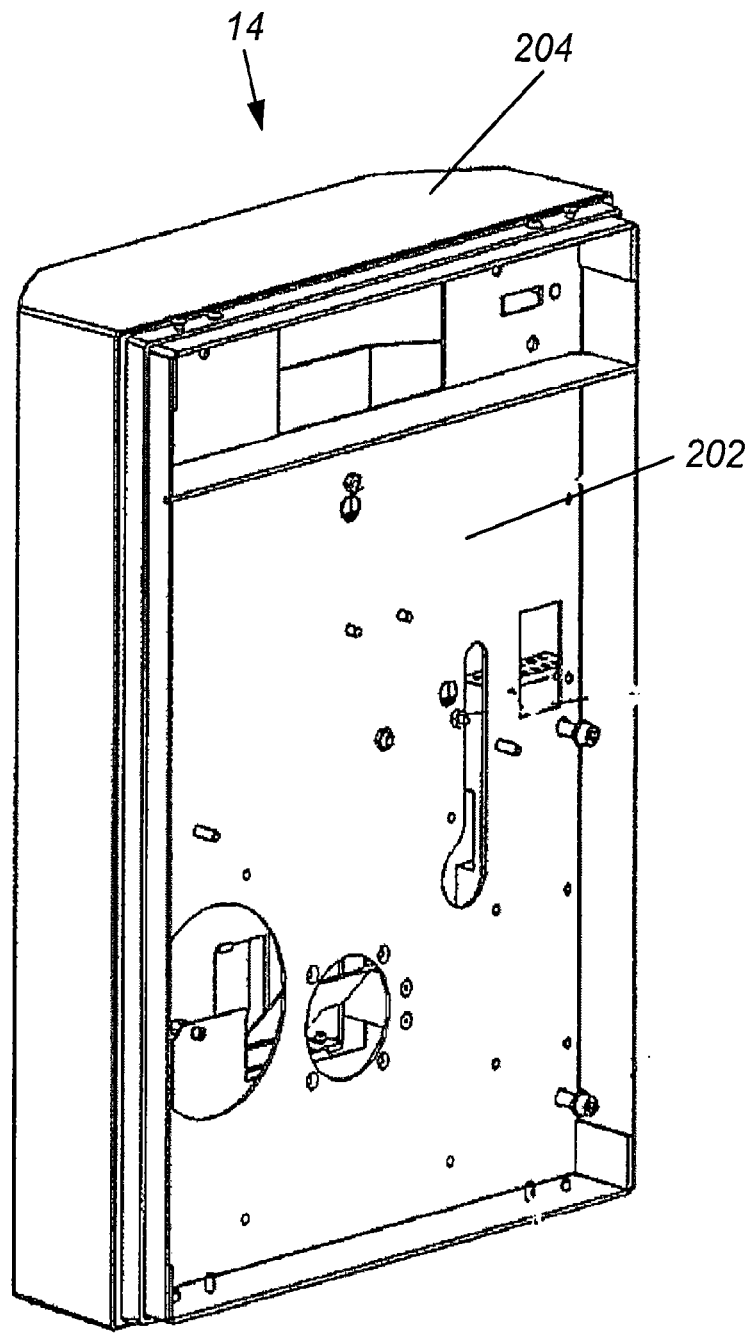
FIG. 15 is a perspective view of a housing of the x-ray source shown in FIG. 14 illustrating a panel that separates a chamber in which an x-ray source is located and a beam limiter or collimator is located.
Figure 16:
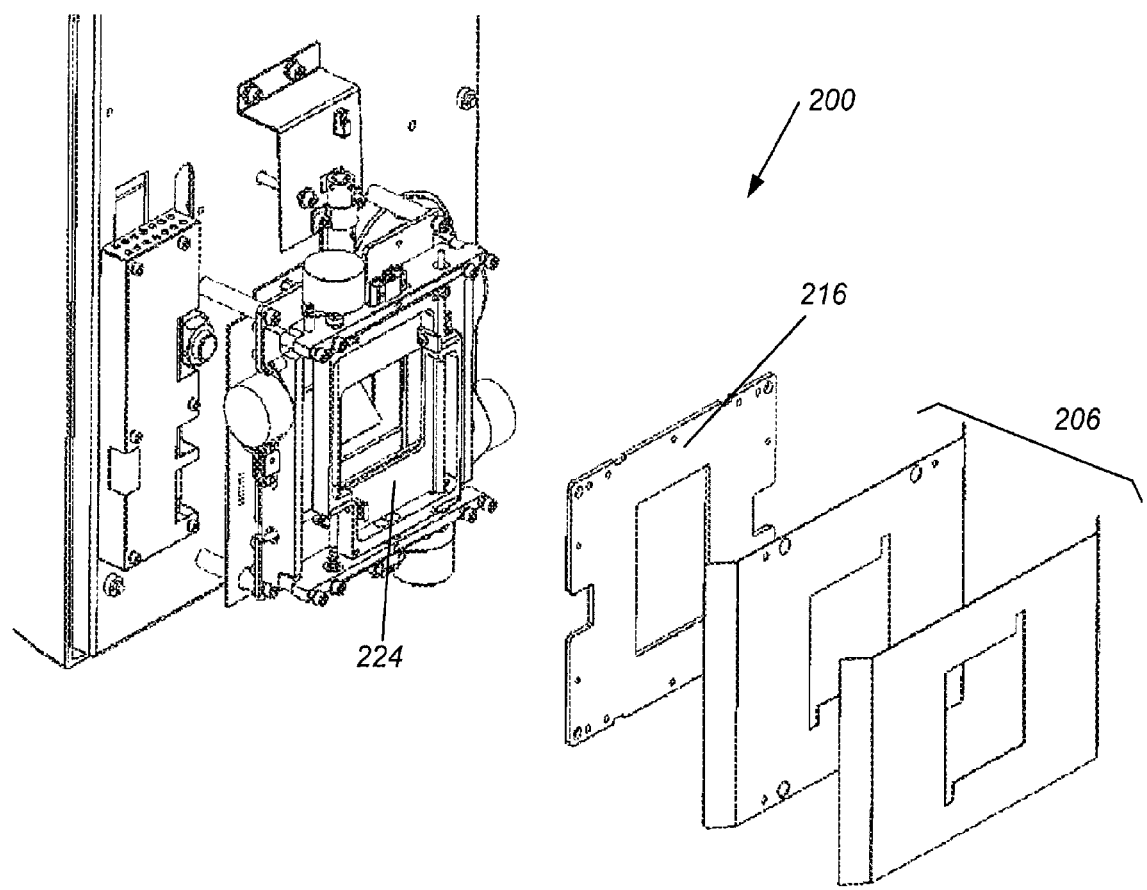
FIG. 16 is a partially exploded view of a collimator illustrating a number of leaves used in a door of the collimator.
Figure 17:
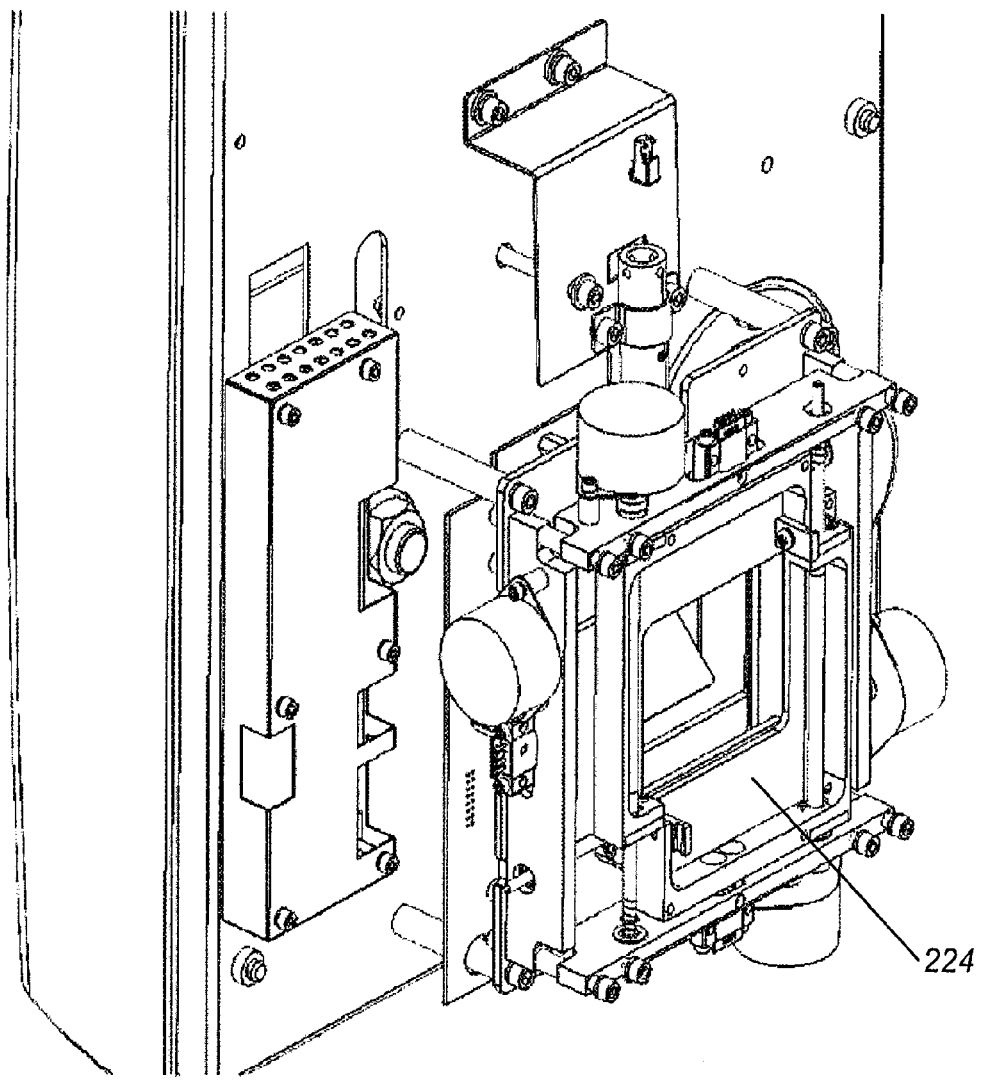
FIG. 17 is a perspective view of the components used to collimate x-rays.
Figure 18:
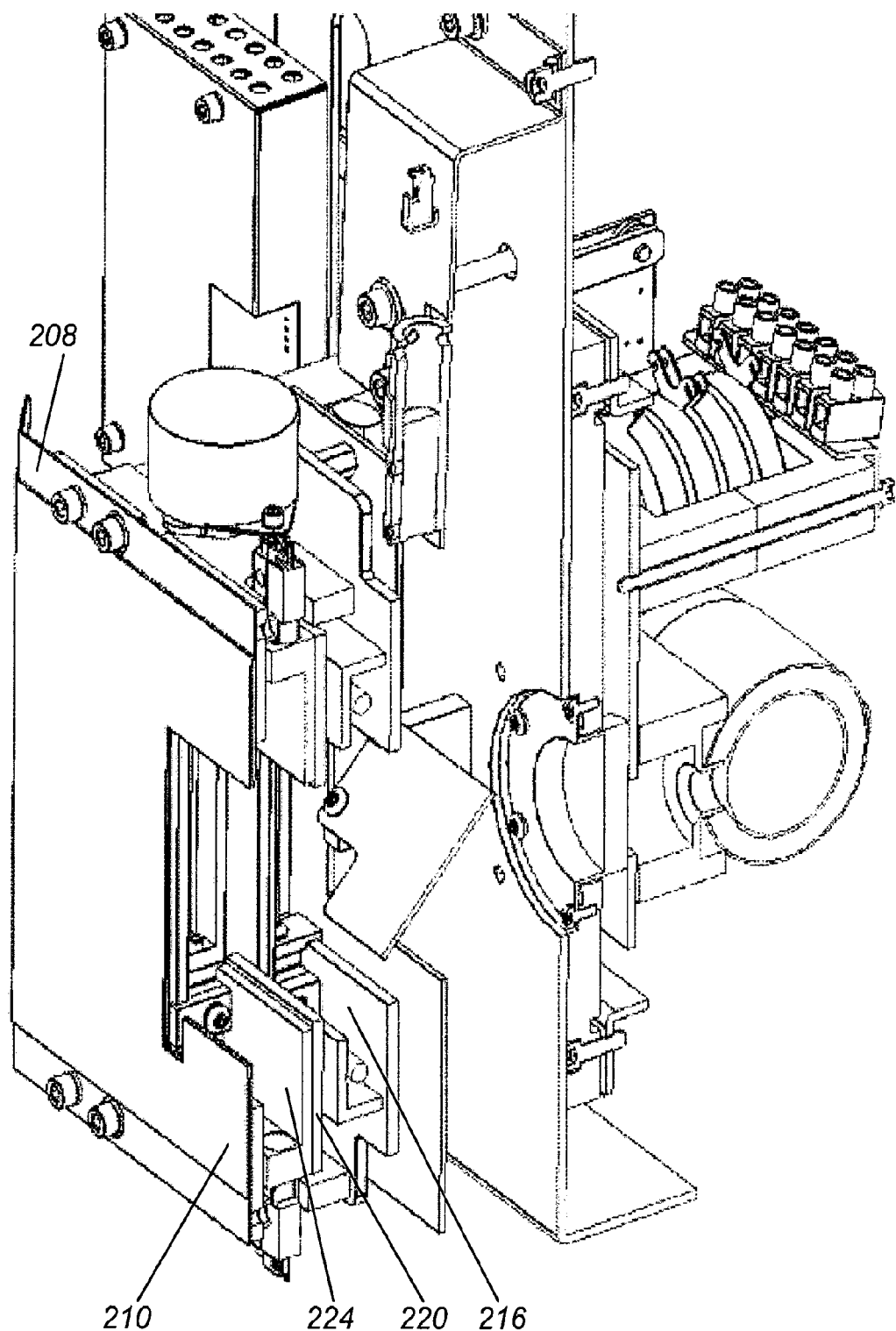
FIG. 18 is a partially cut-away view of doors in the collimator of the prior figures.
Figure 19A:
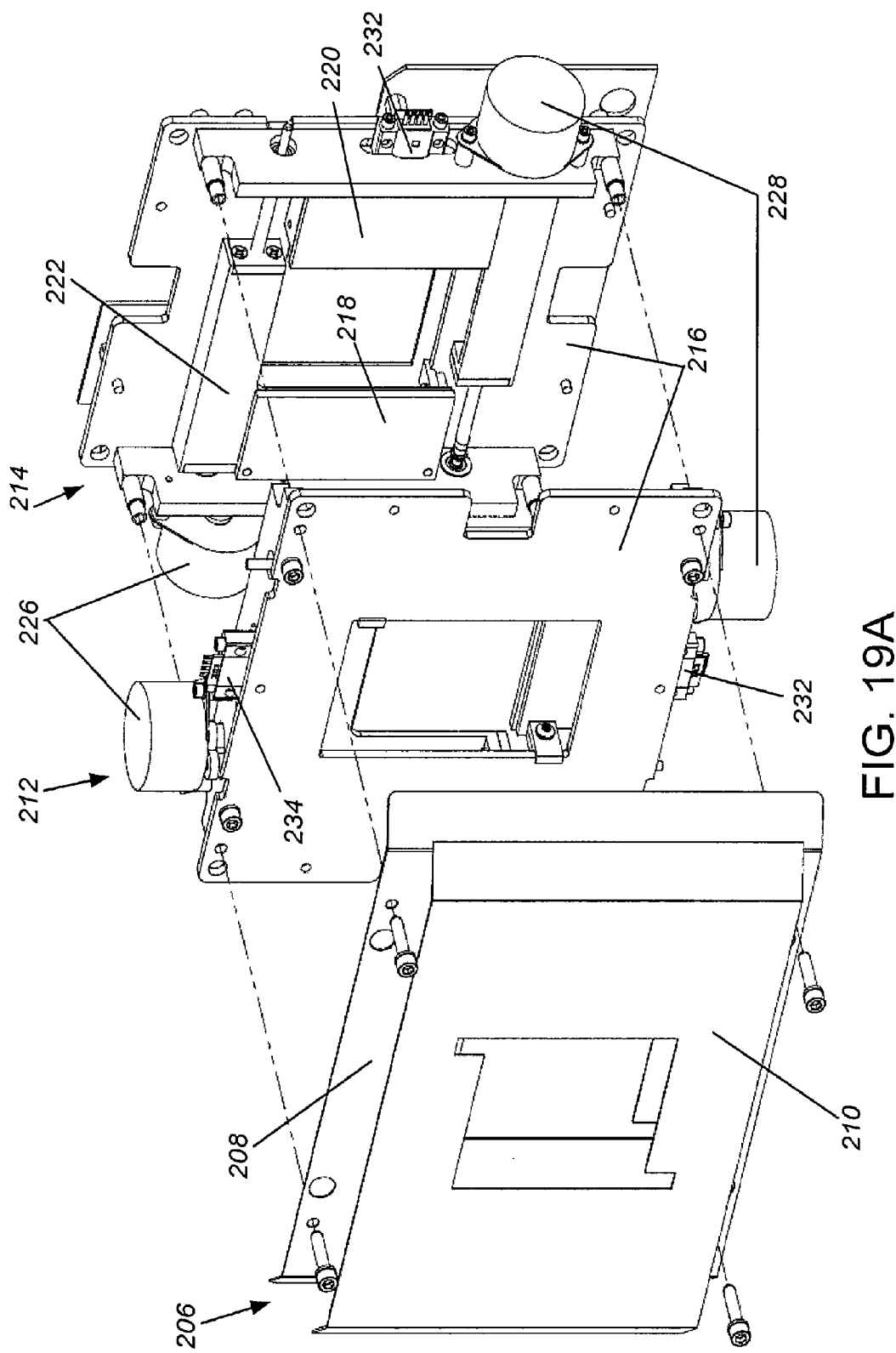
FIG. 19A is an exploded view of a portion of the beam limiter in FIG. 14.
Figure 19B:
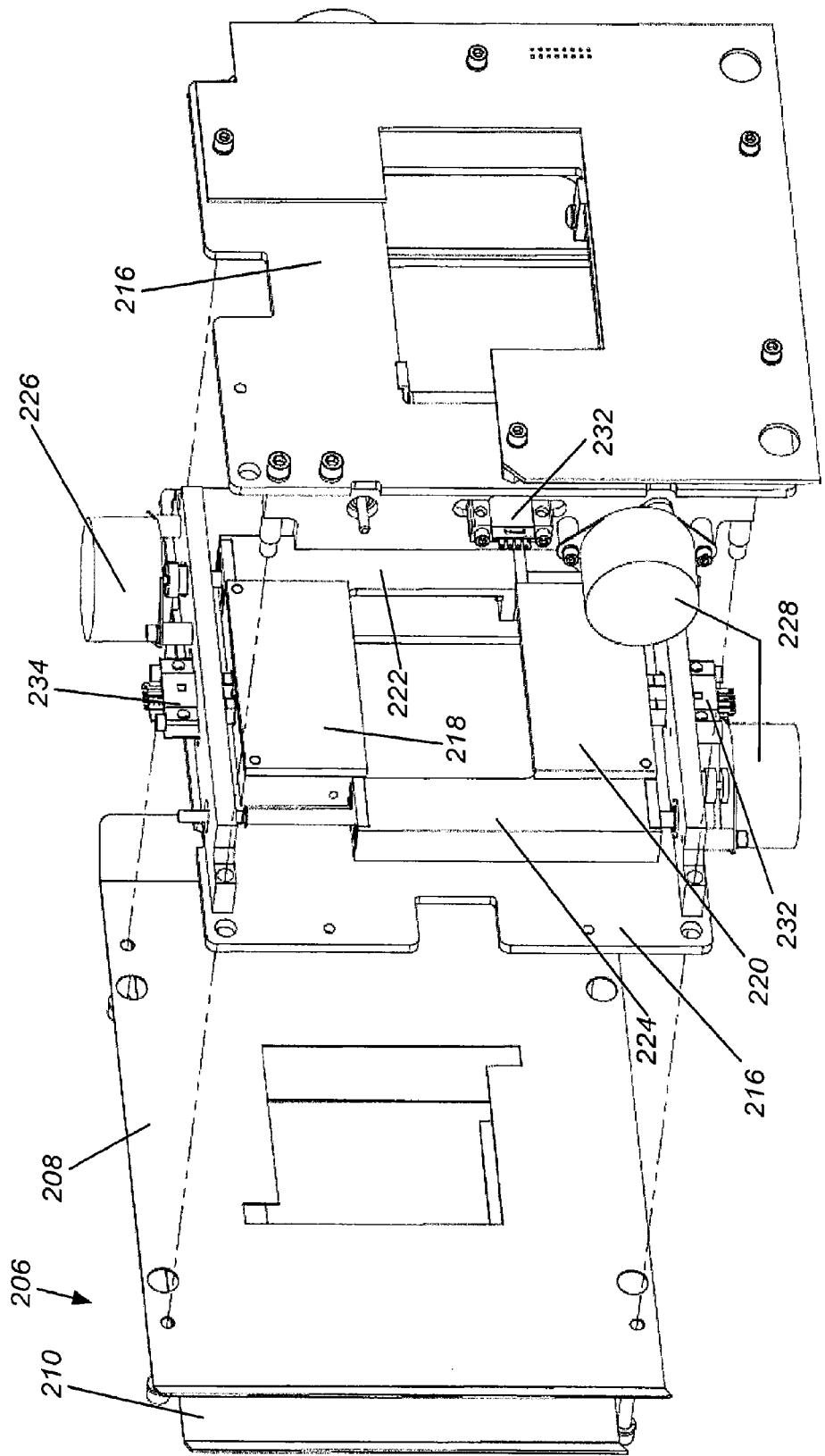
FIG. 19B is another exploded view of the portion of the beam limiter in FIG. 19A.

One embodiment of the beam limiter is illustrated in the attached FIGS. 14 through 19. A beam limiter 200 is shown in FIG. 14. The beam limiter 200 is part of the x-ray source 14 and is attached to a plate 202 located within a housing 204. The embodiment of the beam limiter 200 shown includes a scatter shield structure 206 having scatter shield support plate 208 and a lead scatter shield 210, and two shutter structures 212 and 214. In the illustrated construction, shutter structures 212 and 214 include the same components, thus only one will be described for brevity. For example, shutter structure 212 includes a mounting plate 216 supporting two doors or shutters 218 and 220, each door 218 and 220 being coupled to a corresponding carrier plate 222 and 224 for movement with respect to one another. The carrier plates 222 and 224 are each operated by motors 226 and 228, each connected to a corresponding optical sensor 230 and 232. The optical sensors 230 and 232 generate signals related to the position of the carrier plates 222 and 224 with respect to the sensors 230 and 232 to determine the relative position of the doors 218 and 220 and to move the doors 218 and 220 with respect to one another.

The doors 218 and 220 of both shutter structures 212 and 214 are used to create a window at a controllable location for x-ray to be emitted. In the illustrated construction, the doors 218 and 220 of shutter structure 214 move horizontally in the u direction, and the doors 218 and 220 of shutter structure 212 move vertically in the v direction. Either set of doors can meet to block the source from illuminating the object, or be opened at a desired location. By having one set of doors open and the other partially closed a vertical or horizontal slit-like aperture is created. If the second set of doors is also brought to a partially closed position the length of the slit can be decreased. In this way the slit can be made into a rectangular or square aperture. By controlling the relative positions of the four doors, the rectangle or square can be dynamically moved to a number of different positions in front of the x-ray source 14. By coordinating the movements of the four doors (218 and 220 of both shutter structures 212 and 214) with the movements of the gantry 28 and/or detector 20, a specific part of the object being scanned can be targeted. For example, one tooth area of a jaw. Among reasons for doing this are to limit the x-ray dose to the patient, to limit the amount of x-ray scatter that produces image problems such as a halo, and to decrease the overall amount of data reaching a detector so that processing may be performed more quickly.

The embodiment of the beam limiter 200 described above uses a scatter shield and doors resulting in rectangular of square apertures. However, other geometries are contemplated that could result in apertures of other shapes such as a circular shape.

In other embodiments, the rotation of the detector 20 from portrait to landscape as described by PCT application Ser. No. PCT/US08/51922 filed on Jan. 24, 2008, may be combined with the translations, rotations, and angulations described around the u, v, and w axes of this application. One advantage of such combinations would be to improve speed by reading out only part of the panel. By changing whether the panel is in portrait or landscape mode while it acquires its data, the data can be captured by the portion of the panel that is more easily and thus more quickly read. This can speed up the process which is a desirable feature in all CT scanning applications.

Certain commercially available detector panels suitable for use as the x-ray detector 20 are provided with built-in electronics for a high-resolution panoramic imaging mode, in which the x-ray beam is collimated to a narrow vertical slit, and only the detector pixels in the corresponding part of the detector array are read out. That mode greatly speeds the readout process, by reducing the number of pixels read. However, the available panels support the panoramic slit mode only in landscape orientation. High-resolution, full-face panoramic imaging is not usually needed, but the rotatable x-ray detector 20 of the present device allows switching between operating modes including a 25 cm high full-face scan and the panoramic slit mode where a fixed detector panel, in either orientation, could offer only one of those modes.

Various combinations, modifications and variations can be made in the present invention without departing from the spirit or scope of the invention. Thus, it is intended that the present invention cover combinations, modifications and variations of the embodiments described provided they come within the scope of the appended claims and their equivalents.

As an example, a detector panel with an array of sensors 20 cm by 25 cm has been used. That is only an example, and detector panels of other sizes may be used.

As an example, a x-ray detector 20 positioned with the axis of the bearing 30 equidistant from two edges of the panel, so that the bottom edge and one side edge are at the same positions relative to the gantry in the landscape and portrait modes, has been described. Also described as an example is an x-ray detector 20 positioned with the axis of the bearing 30 equidistant from three edges of the panel, so that the bottom edge and one side edge are in the same positions relative to the gantry in the landscape and portrait modes. Certain reasons for those arrangements have been identified. However, other positions of the x-ray detector 20 relative to the axis of the bearing 30 are possible, and may be desirable for certain purposes or in certain scanner configurations.

FIG. 1 shows that the computer 13 on which the image data are processed and analyzed is connected to the scanner 12. A single computer 13 may both control the scanner 12 and process the data. Alternatively, part or all of the processing may be carried out on a separate computer. The data from the scanner 12 may be transferred from computer to computer in a convenient format, for example the DICOM format, at a convenient stage of the process. The data may, for example, be transferred directly from computer to computer or may, for example, be uploaded to and downloaded from a storage server. The detailed control of the motor 46 and the movement of the x-ray detector 20 may be controlled by a dedicated logic controller in the scanner 12, with the computer 13 or other external controller merely issuing a command to adopt a specified one of the portrait and landscape orientations, and receiving a signal confirming that the x-ray detector 20 is in a specific orientation.

What is claimed is:

1. Apparatus for dental and facial imaging, the apparatus comprising:
   a controller;
   a rotatable gantry;
   a source of penetrating radiation mounted on the gantry and including a beam limiter with a plurality of doors; and
   a detector of penetrating radiation mounted opposite the source on the gantry so that when a head of a patient is positioned between the source and the detector the axis of rotation of the gantry passes through the patient's head;
   wherein the detector is mounted translatably on the gantry between a first position and a second position and includes a first stop positioned at the first position and a second stop positioned at the second position, wherein movement of the detector between the first position and the second position is controlled so that the movement of the detector is slowed in a first direction before the detector reaches the first stop and movement of the detector is slowed in a second direction before the detector reaches the second stop,
   wherein the controller is configured to coordinate movement of the rotatable gantry, the plurality of doors of the beam limiter, and movement of the detector.

2. Apparatus according to claim 1 wherein at least one of the detector or the source is mounted translatably on the gantry in a direction generally perpendicular to the axis of rotation of the gantry.

3. Apparatus according to claim 1 wherein at least one of the detector or the source is mounted translatably on the gantry in a direction generally parallel to the axis of rotation of the gantry.

4. Apparatus according to claim 1 wherein the detector and the source are fixedly aligned on the same axis passing between them.

5. Apparatus according to claim 1, wherein the length of the detector along a long axis is sufficient for full-face CT of a human adult when the long axis is upright relative to the patient's head.

6. Apparatus according to claim 1, arranged to be operated with the axis of rotation of the gantry generally in the direction of local gravitational vertical.

7. Apparatus according to claim 1, wherein the detector is aligned so that with a long axis perpendicular to the axis of rotation of the gantry, the center of the detector is on the center axis of a beam of radiation from the source, which center axis intersects the axis of rotation of the gantry.

8. Apparatus according to claim 1, wherein the detector is mounted so that one corner is in the same position in both positions.

9. Apparatus according to claim 1, further comprising a computing device arranged to receive radiation data from the detector and calculate at least one of voxel data and computed tomography pixel data.

10. Apparatus according to claim 1, wherein the detector is generally rectangular.

11. Apparatus according to claim 1 wherein the detector is a flat-panel detector.

12. Apparatus for dental and facial imaging, the apparatus comprising:
   a rotatable gantry;
   a source of penetrating radiation mounted on the gantry; and
   a detector for the radiation mounted opposite the source on the gantry so that when a head of a patient is positioned between the source and the detector the axis of rotation of the gantry passes through the patient's head;
   wherein the source is mounted rotatably on the gantry.

13. Apparatus according to claim 12 wherein the at least one of the detector or the source is mounted rotatably on the gantry in a direction generally parallel to the axis of rotation of the gantry.

14. Apparatus for dental and facial imaging, the apparatus comprising:
   a rotatable gantry;
   a source of penetrating radiation mounted on the gantry; and
   a detector for the radiation mounted opposite the source on the gantry so that a head of a patient is positioned between the source and the detector when the axis of rotation of the gantry passes through the patient's head;
   wherein at least one of the detector or the source is mounted rotatably on the gantry in a direction generally perpendicular to the axis of rotation of the gantry.

15. Apparatus for dental and facial imaging, the apparatus comprising:
   an angulated rotatable gantry;
   a source of penetrating radiation mounted on the gantry;
   a detector for the radiation mounted opposite the source on the gantry so that when a head of a patient is positioned between the source and the detector the axis of rotation of the gantry passes through the patient's head;

wherein at least one of the detector or the source is mounted lower than the vertical midpoint of the patient's head, and the other of the at least one of the detector or the source is mounted higher than the vertical midpoint of the patient's head.

16. Apparatus according to claim 15 wherein the source is mounted lower than the vertical midpoint of the patient's head.

17. Apparatus according to claim 15 wherein the detector is mounted lower than the vertical midpoint of the patient's head.

18. Apparatus for dental and facial imaging, the apparatus comprising:
- a rotatable gantry;
- a source of penetrating radiation mounted on the gantry;
- a dynamic collimator changing its collimation of the source to trim the penetrating radiation to cover only a specific region of the scan field; and
- a detector for the radiation mounted opposite the source on the gantry so that when a head of a patient is positioned between the source and the detector the axis of rotation of the gantry passes through the patient's head;

wherein at least one of the detector or the source is mounted lower than the vertical midpoint of the patient's head, and the other of the at least one of the detector or the source is mounted higher than the vertical midpoint of the patient's head.

19. Apparatus for dental and facial imaging, the apparatus comprising:
- a telescoping and rotatable gantry;
- a source of penetrating radiation mounted on the gantry;
- a dynamic collimator changing its collimation of the source to trim the penetrating radiation to cover only a specific region of the scan field; and
- a detector for the radiation mounted opposite the source on the gantry, so that a head of a patient is positioned between the source and the detector, with the axis of rotation of the gantry passing through the patient's head;

wherein at least one of the detector or the source is mounted lower than the vertical midpoint of the patient's head, and the other of the at least one of the detector or the source is mounted higher than the vertical midpoint of the patient's head.

* * * * *

UNITED STATES PATENT AND TRADEMARK OFFICE
CERTIFICATE OF CORRECTION

PATENT NO.       : 8,503,603 B2                                                                Page 1 of 1
APPLICATION NO.  : 12/918558
DATED            : August 6, 2013
INVENTOR(S)      : Tancredi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 167 days.

Signed and Sealed this
Fifteenth Day of September, 2015

Michelle K. Lee
*Director of the United States Patent and Trademark Office*